US00RE49280E

(19) United States
(12) Reissued Patent
Hinck et al.

(10) Patent Number: US RE49,280 E
(45) Date of Reissued Patent: Nov. 8, 2022

(54) TGFBETA TYPE II-TYPE III RECEPTOR FUSIONS

(71) Applicant: THE BOARD OF REGENTS OF THE UNIVERSITY OF TEXAS SYSTEM, Austin, TX (US)

(72) Inventors: Andrew Hinck, Pittsburg, PA (US); Luzhen Sun, San Antonio, TX (US); Christian Zwieb, San Antonio, TX (US)

(73) Assignee: Board of Regents, The University of Texas System, Austin, TX (US)

(21) Appl. No.: 16/375,242

(22) Filed: Apr. 4, 2019

Related U.S. Patent Documents

Reissue of:

(64) Patent No.: 9,611,306
Issued: Apr. 4, 2017
Appl. No.: 14/387,901
PCT Filed: Mar. 28, 2013
PCT No.: PCT/US2013/034504
§ 371 (c)(1),
(2) Date: Sep. 25, 2014
PCT Pub. No.: WO2013/149094
PCT Pub. Date: Oct. 3, 2013

U.S. Applications:

(60) Provisional application No. 61/616,740, filed on Mar. 28, 2012.

(51) Int. Cl.

| | |
|---|---|
| ***C07K 14/00*** | (2006.01) |
| ***C12N 15/85*** | (2006.01) |
| ***C07K 14/495*** | (2006.01) |
| ***C07K 14/71*** | (2006.01) |
| ***C12N 15/64*** | (2006.01) |

(52) U.S. Cl.
CPC ..... *C07K 14/495* (2013.01); *C07K 14/71* (2013.01); *C12N 15/64* (2013.01); *C07K 2319/32* (2013.01)

(58) Field of Classification Search
None
See application file for complete search history.

(56) References Cited

U.S. PATENT DOCUMENTS

| | | | | |
|---|---|---|---|---|
| 9,376,463 | B2 * | 6/2016 | Kyhse-Andersen | C07K 1/22 |
| 2002/0004037 | A1 | 1/2002 | Koteliansky et al. | 424/85.1 |
| 2007/0154994 | A1 | 7/2007 | De Crescenzo et al. | 435/69.7 |
| 2007/0184052 | A1 | 8/2007 | Lin et al. | 424/145.1 |
| 2007/0244042 | A1 * | 10/2007 | Sun | C07K 14/71 530/350 |
| 2010/0204104 | A1 | 8/2010 | Qiu et al. | 514/1.1 |

FOREIGN PATENT DOCUMENTS

WO WO 2013/149094 10/2013

OTHER PUBLICATIONS

Extended European Search Report in European Application No. 13768513.7 dated Dec. 17, 2016.
International Search Report and Written Opinion issued in PCT/US15/40345, dated Oct. 16, 2015.
International Search Report and Written Opinion issued in PCT/US2013/034504, dated Jun. 19, 2013.
Wang et al., "Development of gene-switch transgenic mice that inducibly express transforming growth factor beta 1 in the epidermis", *Proc Natl Acad Sci USA*, 96: 8483-8488, 1999.
Bandyopadhyay et al. Antitumor activity of a recombinant soluble betaglycan in human breast cancer xenograft. Cancer Res. Aug. 15, 2002;62(16):4690-5.*
Adler et al., "Elevated levels of circulating interleukin-6 and transforming growth factor-beta 1 in patients with metastatic prostatic carcinoma", *J Urol*, 161: 182-187, 1999.
Arteaga et al., "The multifunctional role of transforming growth factor (TGF)-beta s on mammary epithelial cell biology", *Breast Cancer Res Treat*, 38: 49-56, 1996.
Baardsnes et al., "TbetaR-II discriminates the high- and low-affinity TGF-beta isoforms via two hydrogen-bonded ion pairs", *Biochemistry*, 48: 2146-55, 2009.
Bandyopadhyay et al., "A soluble transforming growth factor beta type III receptor suppresses tumorigenicity and metastasis of human breast cancer MDA-MB-231 cells", *Cancer Res.*, 59: 5041-5046, 1999.
Bandyopadhyay et al., "Antitumor activity of a recombinant soluble betaglycan in human breast cancer xenograft", *Cancer Res.*, 62: 4690-4695, 2002a.
Bandyopadhyay et al., "Extracellular domain of TGFbeta type III receptor inhibits angiogenesis and tumor growth in human cancer cells", *Oncogene*, 21: 3541-3551, 2002b.
Extended European Search Report in European Application No. 13768513.7 dated Dec. 17, 2015.
Hinck and O'Connor-McCourt, "Structures of TGG-beta receptor complexes: implications for function and therapeutic intervention using ligand traps" Curr Pharm Biotech. 12: 2081-98, 2011.
Koeneman et al., "Osteomimetic properties of prostate cancer cells: a hypothesis supporting the predilection of prostate cancer metastasis and growth in the bone environment", *Prostate*, 39: 246-261, 1999.
Lee et al., "Transforming growth factor-beta in benign and malignant prostate", *Prostate*, 39: 285-290, 1999.

(Continued)

*Primary Examiner* — Celine X Qian

(57) ABSTRACT

Certain embodiments are directed to novel heterotrimeric fusions in which the ectodomain of the TGF-β type II receptor (TβP?II) is coupled to the N- and C-terminal ends of the endoglin-domain of the TGF-β type III receptor (TpRIIIE). Certain embodiments are directed to novel heterotrimeric polypeptides in which the ectodomain of the TGF-β type II receptor (TI3RII) is coupled to the N- and C-terminal ends of the endoglin-domain (E domain) of the TGF-β type III receptor (TI3RIII). This trimeric receptor, known as RER, can bind all three TGF-β isoforms with sub-nanomolar affinity and is effective at neutralizing signaling induced by all three TGF-β isoforms, but not other ligands of the TGF-β superfamily, such as activins, growth and differentiation factors (GDFs), and bone morphonogenetic proteins (BMPs).

43 Claims, 9 Drawing Sheets

Specification includes a Sequence Listing.

(56) References Cited

OTHER PUBLICATIONS

Lin et al., "The soluble exoplasmic domain of the type II transforming growth factor (TGF)-beta receptor. A heterogeneously glycosylated protein with high affinity and selectivity for TGF-beta ligands", *J Biol Chem.*, 270: 2747-2754, 1995.
Lyons and Moses, "Transforming growth factors and the regulation of cell proliferation", *Eur J Biochem*, 187: 467-473, 1990.
Markowitz and Roberts, "Tumor suppressor activity of the TGF-beta pathway in human cancers", *Cytokine*, Growth Factor, Rev., 7: 93-102, 1996.
Massague et al., "TGFbeta signaling in growth control, cancer, and heritable disorders", *Cell*, 103: 295-309, 2000.
Mendoza et al., "Betaglycan has two independent domains required for high affinity TGF-beta binding: proteolytic cleavage separates the domains and inactivates the neutralizing activity of the soluble receptor", *Biochemistry*, 48(49): 11755-11765, 2009.
Radaev et al., "Ternary complex of transforming growth factor-beta 1 reveals isoform-specific ligand recognition and receptor recruitment in the superfamily", *Journal of Biological Chemistry*, 285: 14806-14, 2010.
Reiss, "TGF-beta and cancer", *Microbes and Infection*, 1: 1327-1347, 1999.
Roberts and Wakefield, "The two faces of transforming growth factor beta in carcinogenesis", *Proc Natl Acad Sci USA*, 100: 8621-8623, 2003.
Shariat et al., "Preoperative plasma levels of transforming growth factor beta(1) (TGF-beta(1)) strongly predict progression in patients undergoing radical prostatectomy", *J Clin Oncol*, 19: 2856-2864, 2001.
Verona, et al., "Expression, purification and characterization of BGeRII: a novel pan-TGFbeta inhibitor" Protein Engineering Design and Selection. 21(7):463-23, 2008.
Vilchis-Landeros et al., "Recombinant soluble betaglycan is a potent and isoform-selective transforming growth factor-beta neutralizing agent", *Biochem J.*, 355: 215-222, 2001.
Yin et al., "TGF-beta signaling blockade inhibits PTHrP secretion by breast cancer cells and bone metastases development", *J Clin Invest*, 103: 197-206, 1999.

* cited by examiner

| Neutralization potency of various TGF-β inhibitors in a mink lung epithelial cell (Mv1Lu) luciferase reporter gene assay | | | |
|---|---|---|---|
| | | | |
| | $IC_{50}$ (nM) | $IC_{50}$ Std. Dev. (nM) | Number of measurements |
| RR (RII-RII) | | | |
| TGF-β1 | 1.5 | 0.8 | 4 |
| TGF-β2 | n.d. | n.d. | 4 |
| TGF-β3 | 0.27 | 0.22 | 4 |
| RER (RII-$BG_E$-RII) | | | |
| TGF-β1 | 0.00051 | 0.00022 | 3 |
| TGF-β2 | 0.070 | 0.018 | 3 |
| TGF-β3 | 0.0033 | 0.0058 | 3 |
| ER ($BG_E$-RII) | | | |
| TGF-β1 | 0.014 | 0.009 | 2 |
| TGF-β2 | 1.2 | 0.3 | 2 |
| TGF-β3 | 0.020 | 0.011 | 2 |
| REU (RII-$BG_E$-$BG_U$, or RII-RIII) | | | |
| TGF-β1 | 0.18 | 0.04 | 2 |
| TGF-β2 | 0.81 | 0.10 | 2 |
| TGF-β3 | 0.067 | 0.021 | 2 |
| EU ($BG_E$-$BG_U$, or RIII) | | | |
| TGF-β1 | n.d. | n.d. | 2 |
| TGF-β2 | n.d. | n.d. | 2 |
| TGF-β3 | n.d. | n.d. | 2 |
| 1D11 (Genzyme's pan isoform specific TGF-β neutralizing antibody) | | | |
| TGF-β1 | 0.99 | 0.98 | 2 |
| TGF-β2 | 5.5 | 1.0 | 2 |
| TGF-β3 | 0.093 | 0.016 | 2 |

FIG. 6

TGFBETA TYPE II-TYPE III RECEPTOR FUSIONS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

PRIORITY PARAGRAPH

This application is a U.S. National Stage Application of International Application serial number PCT/US2013/034504 filed Mar. 28, 2013, which claims priority to U.S. Provisional Application serial number 61/616,740 filed Mar. 28, 2012. This application claims priority to and incorporates by reference each of the above referenced applications in their entirety.

STATEMENT REGARDING FEDERALLY FUNDED RESEARCH

This invention was made with government support under CA079683 and GM58670 awarded by the National Institutes of Health. The government has certain rights in the invention.

REFERENCE TO SEQUENCE LISTING

A sequence listing is being submitted electronically with this application. The sequence listing is incorporated herein by reference.

BACKGROUND

Transforming growth factor beta (TGFβ) isoforms (β1, β2, and β3) are homodimeric polypeptides of 25 kDa. They are secreted in a latent form and only a small percentage of total secreted TGFβs are activated under physiological conditions. TGFβ binds to three different cell surface receptors called type I (RI), type II (RII), and type III (RIII) receptors. RI and RII are serine/threonine kinase receptors. RIII (also called betaglycan) has two TGFβ binding sites in its extracellular domain, which are called the E and U domains ($BG_E$ and $BG_U$, respectively). TGFβ1 and TGFβ3 bind RII with an affinity that is 200-300 fold higher than TGF-β2 (Baardsnes et al., Biochemistry, 48, 2146-55, 2009); accordingly, cells deficient in RIII are 200- to 300-fold less responsive to equivalent concentrations of TGF-β2 compared to TGF-β1 and TGFβ-3 (Chiefetz, et al (1990) J. Bio. Chem., 265, 20533-20538). However, in the presence of RIII, cells respond roughly equally to all three TGF-β isoforms, consistent with reports that show that RIII can sequester and present the ligand to RII to augment TGFβ activity when it is membrane-bound (Chen et al., J. Biol. Chem. 272, 12862-12867, 1997; Lopez-Casillas et al., Cell 73, 1435-1444, 1993; Wang et al., Cell 67, 797-805, 1991; Fukushima et al., J. Biol. Chem. 268, 22710-22715, 1993; Lopez-Casillas et al., J. Cell Biol. 124, 557-568, 1994). Binding of TGFβ to RII recruits and activates RI through phosphorylation (Wrana et al., Nature 370, 341-347, 1994). The activated RI phosphorylates intracellular Smad2 and Smad3, which then interact with Smad4 to regulate gene expression in the nucleus (Piek et al., FASEB J. 13, 2105-2124, 1999; Massague and Chen, Genes & Development 14, 627-644, 2000).

Through its regulation of gene expression, TGFβ has been shown to influence many cellular functions such as cell proliferation, cell differentiation, cell-cell and cell-matrix adhesion, cell motility, and activation of lymphocytes (Massague, Ann. Rev. Cell Biol. 6, 597-641, 1990; Roberts and Sporn, The transforming growth factor-betas. In Peptide growth factors and their receptors I, Sporn and Roberts, eds. (Heidelberg: Springer-Verlag), pp. 419-472, 1991). TGFβ has also been shown or implicated in inducing or mediating the progression of many diseases such as osteoporosis, hypertension, atherosclerosis, hepatic cirrhosis and fibrotic diseases of the kidney, liver, and lung (Blobe et al., N. Engl. J. Med. 342, 1350-1358, 2000). Perhaps, the most extensively studied function of TGFβ is its role in tumor progression.

TGFβs have been shown to be potent growth inhibitors in various cell types including epithelial cells (Lyons and Moses, Eur. J. Biochem. 187, 467-473, 1990). The mechanism of the growth inhibition by TGFβ is mainly due to the regulation of cell cycle-related proteins (Derynck, Trends. Biochem. Sci. 19, 548-553, 1994; Miyazono et al., Semin. Cell Biol. 5, 389-398, 1994). Thus, aberrant regulation of cell cycle machinery such as loss of retinoblastoma gene product during tumorigenesis can lead to loss of growth inhibition by TGFβ. Furthermore, mutational inactivation of TGFβ receptors, Smad2, and Smad4 has been reported in various carcinomas (Massague et al., Cell 103, 295-309, 2000). For example, loss of RI and/or RII expression is often observed in some human gastrointestinal cancers (Markowitz and Roberts, Cytokine, Growth Factor, Rev. 7, 93-102, 1996).

While many carcinoma cells lose response to TGFβ's growth inhibition, they often overproduce active TGFβ isoforms when compared to their normal counterpart (Reiss, Microbes and Infection 1, 1327-1347, 1999). This is likely to result in the selection of cancer cells that are resistant to TGFβ's growth inhibitory activity. Indeed, an increased level of TGFβ1 is strongly associated with the progression of many types of malignancies and poor clinical outcome (Reiss, Microbes and Infection 1, 1327-1347, 1999). For example, serum TGFβ1 levels have been shown to correlate to tumor burden, metastasis, and serum prostate specific antigen (PSA) in prostate cancer patients (Adler et al., J. Urol. 161, 182-187, 1999; Shariat et al., J. Clin. Oncol. 19, 2856-2864, 2001). Consistent with these observations, marked increase of TGFβ1 and TGFβ2 expression was observed in an aggressive androgen-independent human prostate cancer cell line when compared to its less aggressive androgen-dependent parent cell line, LNCap (Patel et al., J. Urol. 164, 1420-1425, 2000).

Several mechanisms are believed to mediate TGFβ's tumor-promoting activity (Arteaga et al., Breast Cancer Res. Treat. 38, 49-56, 1996; Reiss, Microbes and Infection 1, 1327-1347, 1999). TGFβ is a potent immune suppressor (Sosroseno and Herminajeng, Br. J. Biomed. Sci. 52, 142-148, 1995). Overexpression of TGFβ1 in the rat prostate cancer cells was associated with a reduced immune response during tumor formation suggesting that TGFβ may suppress host immune response to the growing tumor (Lee et al., Prostate 39, 285-290, 1999). TGFβ has also been shown to be angiogenic in vivo (Fajardo et al., Lab. Invest. 74, 600-608, 1996; Yang and Moses, J. Cell Biol. 111, 731-741, 1990; Wang et al., Proc. Natl. Acad. Sci. U.S.A. 96, 8483-8488, 1999). Overexpression of TGFβ during cancer progression is often associated with increased angiogenesis and metastasis suggesting that TGFβ may promote metastasis by stimulating tumor blood vessel formation (Roberts and Wakefield, Proc. Natl. Acad. Sci. U.S.A. 100, 8621-8623, 2003). TGFβ also plays an important role in promoting bone metastasis of human prostate and breast cancers (Koeneman et al., Prostate 39, 246-261, 1999; Yin et al., J. Clin. Invest 103, 197-206, 1999). Both TGFβ1 and TGFβ2 are produced by bone tissue, which is the largest source of TGFβ in the body (Bonewald and Mundy, Clin. Orthop. 261-276, 1990). The latent TGFβ can be activated by proteases such as PSA and urokinase plasminogen activator, which are abundantly secreted by cancer cells (Koeneman et al., Prostate 39, 246-261, 1999). Taken together, TGFβ can act in tumor microenvironment to promote carcinoma growth, angiogenesis, and metastasis.

Because of its involvement in the progression of various diseases, TGFβ has been targeted for the development of novel therapeutic strategies. One way of antagonizing TGFβ activity is to utilize the ectodomain of TGFβ type II receptor or type III receptor (betaglycan (BG)). It has previously been shown that ectopic expression of a soluble RIII (sBG) in human carcinoma cell lines can significantly inhibit tumor growth, angiogenesis, and metastasis when they are inoculated in athymic nude mice (Bandyopadhyay et al., Cancer Res. 59, 5041-5046, 1999; Bandyopadhyay et al., Oncogene 21, 3541-3551, 2002b). More recently, it has been shown that systemic administration of recombinant sRIII can inhibit the growth, angiogenesis, and metastasis of the xenografts of human breast carcinoma MDA-MB-231 cells in nude mice (Bandyopadhyay et al., Cancer Res. 62, 4690-4695, 2002a). However, the inhibition was only partial. This could be due, in part, to the fact that the cells produced active TGFβ1 and active TGFβ2 and the anti-TGFβ potency of sRIII is 10-fold lower for TGFβ1 than for TGFβ2 (Vilchis-Landeros et al., Biochem. J. 355, 215-222, 2001). Interestingly, while the extracellular domain of RII (sRII) has very low affinity for TGFβ2, its affinity for TGFβ1 and TGFβ3 is more than ten times higher than that of sRIII (Lin et al., J. Biol. Chem. 270, 2747-2754, 1995; Vilchis-Landeros et al., Biochem. J. 355, 215-222, 2001).

While numerous TGFβ antagonists have been prepared and tested, all have less than complete TGFβ isoform inhibiting properties. Thus, there is a need for additional TGF antagonists or inhibitors.

SUMMARY

Certain embodiments are directed to novel heterotrimeric polypeptides in which the ectodomain of the TGF-β type II receptor (TβRII) is coupled to the N- and C-terminal ends of the endoglin-domain (E domain) of the TGF-β type III receptor (TβRIII). This trimeric receptor, known as RER, can bind all three TGF-β isoforms with sub-nanomolar affinity and is effective at neutralizing signaling induced by all three TGF-β isoforms, but not other ligands of the TGF-β superfamily, such as activins, growth and differentiation factors (GDFs), and bone morphonogenetic proteins (BMPs). The sub-nanomolar affinity of the fusion, which arises from its ability to contact the TGF-β dimer at three distinct sites, allows it to effectively compete against the endogenous receptors for TGF-β binding. The fusion proteins described herein offer significant potential as a therapeutic agent for treating diseases driven by overexpression of the TGF-β isoforms, such as cancer and fibrosis.

Certain aspects are directed to a heterotrimeric fusion protein comprising (a) an amino terminal segment comprising a first TGFβ binding domain of TGFβ receptor type II, (b) a central segment comprising a endoglin-domain of TGFβ receptor type III, and (c) a carboxy terminal segment comprising a second TGFβ binding domain of TGFβ receptor type II.

An example of a TGFβ type II receptor is provided as SEQ ID NO:6. Amino acids 1 to 567 of SEQ ID NO:6 is a TGFβ receptor type-2 precursor (EC_number=2.7.11.30). The signal peptide is composed of amino acid 1 to 22 of SEQ ID NO:6. The mature peptide includes amino acids 23 to 567 of SEQ ID NO:6. The ectodomain is defined by amino acids 24 to 160 of SEQ ID NO:6 (RII domain). The ectodomain is followed by a transmembrane region that spans amino acids 161 to 187 of SEQ ID NO:6. The amino terminal segment or the carboxy terminal segment of a novel heterotrimeric fusion protein described herein can comprise, independently, an amino acid segment that is 85, 90, 95, 98, or 100% identical, including all values and ranges there between, to amino acids 35, 40, 41, 42, 43, 44, 45, 46, 47, 48, 49, 50, 55, 60, 65, 70, or 75 to 145, 150, 155, 160, 161, 162, 163, 164, 165, 166, 167, 168, 169, or 170 of SEQ ID NO:6, including all values and ranges there between. The polypeptide segment's ability to bind TGFβ can be determined by using standard ligand binding assays known to those of skill in the art. In certain aspects the RII domain comprises point mutations that alter the binding affinity of the RII domain or the binding affinity of a polypeptide comprising an RII domain. In certain aspects amino acid residues 27, 30, 32, 50, 51, 52, 53, 55, 118, and 119 can be altered singly or in various combinations.

An example of a TGFβ type III receptor is provided as SEQ ID NO:7 or SEQ ID NO:8. Amino acids 1 to 23 of SEQ ID NO:7 or 1 to 21 of SEQ ID NO:8 define the signal peptide. Amino acids 24-409 of SEQ ID NO:7 or 21-406 of SEQ ID NO:8 define the endoglin-like domain (E domain or region), amino acids 410 to 783 of SEQ ID NO:7 or 407-780 of SEQ ID NO:8 define the zona pellucida-like domain or uromodulin-like domain (U domain or region), and amino acids 789 to 811 of SEQ ID NO:7 or 786 to 808 of SEQ ID NO:8 define the transmembrane region. The central segment of the trimeric fusion protein can comprise an amino acid segment that is 85, 90, 95, 98, or 100% identical, including all values and ranges there between, to amino acids 21, 22, 23, 24, 25, 26, 27, 28, 29, 30, 31, 32, 33, 34, 35, 36, 37, 38, 39, 40, 45, 50, or 60 to 350, 355, 360, 361, 362, 364, 365, 370, 375, 380, 385, 390, 395, 400, 405 or 409 of SEQ ID NO:7 or SEQ ID NO:8, including all values and ranges there between. In certain aspects the E domain comprises point mutations that alter the binding affinity of the E domain or the binding affinity of a polypeptide comprising an E domain. In another embodiment, the central segment of the trimeric fusion protein can comprise an amino acid segment that is 85, 90, 95, 98, or 100% identical, including all values and ranges there between, to amino acids 405, 410, 415, 420, 425, 430, 440, 445, 450, 460, 470, 480, 490, 500, 510, 520, 530, 540, or 550 to 500, 510, 520, 530, 540, 550, 560, 570, 580, 590, 600, 610, 620, 630, 640, 650, 660, 670, 690, 700, 710, 720, 730, 740, 750, 760, 770, or 780 of SEQ ID NO:7 or SEQ ID NO:8, including all values and ranges there between. The polypeptide segment's ability to bind TGFβ can be determined by using standard ligand binding assays known to those of skill in the art. In certain aspects amino acid 69, 71, 72, 90, 93, 99, 108, 115, 120, 144, 163, 192, 206, 237, 252, 274, 283, and 336 of SEQ ID NO:7 can be altered singly or in various combinations, or the corresponding amino acids of SEQ ID NO:8.

In certain aspects, the fusion protein can further comprise a linker between the amino terminal segment and the central segment, and/or a linker between the central segment and the carboxy terminal segment. In a further aspect, the linkers can comprise 1, 2, 3, 4, 5, 6, 7, 8, 9, 10, 11, 12, 13, 14, 15, 16, 17, 18, 19, 20 or more amino acids. In certain aspects, the amino acids of the linker are additional TGFβ receptor type II or type III amino acid sequences. In other aspects, the linkers are not TGFβ receptor type II or type III amino acid sequences, i.e., heterologous linkers.

In certain aspects, the amino terminal segment comprises an amino acid sequence that is 85, 90, 95, 98, or 100% identical to SEQ ID NO:3, including all values and ranges there between.

In a further aspect, the central segment comprises an amino acid sequence that is 85, 90, 95, 98, or 100% identical to SEQ ID NO:4, including all values and ranges there between.

In yet a further aspect, the carboxy terminal segment comprises an amino acid sequence that is 85, 90, 95, 98, or 100% identical to SEQ ID NO:5, including all values and ranges there between.

In certain aspects, the fusion protein has an amino acid sequence that is 85, 90, 95, 98, or 100% identical to SEQ ID NO:2, including all values and ranges there between.

In a further aspect, the fusion protein can further comprise an amino terminal signal sequence. In certain aspects, the fusion protein can further comprise an amino terminal or carboxy terminal tag. In certain aspects the tag is hexa-histidine.

A peptide tag as used herein refers to a peptide sequence that is attached (for instance through genetic engineering) to another peptide or a protein, to provide a function to the resultant fusion. Peptide tags are usually relatively short in comparison to a protein to which they are fused; by way of example, peptide tags are four or more amino acids in length, such as, 5, 6, 7, 8, 9, 10, 15, 20, or 25 or more amino acids. Usually a peptide tag will be no more than about 100 amino acids in length, and may be no more than about 75, no more than about 50, no more than about 40, or no more than about 30.

Peptide tags confer one or more different functions to a fusion protein (thereby "functionalizing" that protein), and such functions can include (but are not limited to) antibody binding (an epitope tag), purification, translocation, targeting, and differentiation (e.g., from a native protein). In addition, a recognition site for a protease, for which a binding antibody is known, can be used as a specifically cleavable epitope tag. The use of such a cleavable tag can provide selective cleavage and activation of a protein. Alternatively the system developed by in the Dowdy laboratory (Vocero-Akbani et al, Nat. Med. 5:29-33, 1999) could be use to provide specificity of such cleavage and activation.

Detection of the tagged molecule can be achieved using a number of different techniques. These include: immunohistochemistry, immunoprecipitation, flow cytometry, immunofluorescence microscopy, ELISA, immunoblotting ("western"), and affinity chromatography.

Epitope tags add a known epitope (antibody binding site) on the subject protein, to provide binding of a known and often high-affinity antibody, and thereby allowing one to specifically identify and track the tagged protein that has been added to a living organism or to cultured cells. Examples of epitope tags include the myc, T7, GST, GFP, HA (hemagglutinin) and FLAG tags. The first four examples are epitopes derived from existing molecules. In contrast, FLAG is a synthetic epitope tag designed for high antigenicity (see, e.g., U.S. Pat. Nos. 4,703,004 and 4,851,341).

Purification tags are used to permit easy purification of the tagged protein, such as by affinity chromatography. A well-known purification tag is the hexa-histidine (6× His) tag, literally a sequence of six histidine residues. The 6× His protein purification system is available commercially from QIAGEN (Valencia, Calif.), under the name of QIAexpress®.

Certain embodiments are directed to the therapeutic use of the fusions proteins described herein. Certain aspects are directed to a method of treating a TGFβ related condition comprising administering an effective amount of a fusion protein described herein. The fusion protein can be administered to a subject, such as a mammal. The mammal being treated may have or may be at risk for one or more conditions associated with an excess of TGF-β for which a reduction in TGF-β levels may be desirable. Such conditions include, but are not limited to, fibrotic diseases (such as glomerulonephritis, neural scarring, dermal scarring, pulmonary fibrosis (e.g., idiopathic pulmonary fibrosis), lung fibrosis, radiation-induced fibrosis, hepatic fibrosis, myelofibrosis), peritoneal adhesions, hyperproliferative diseases (e.g., cancer), burns, immune-mediated diseases, inflammatory diseases (including rheumatoid arthritis), transplant rejection, Dupuytren's contracture, and gastric ulcers. In certain aspects the fusion protein is administer intravascularly.

Other terms related to the description provided herein include:

The term "receptor" denotes a cell-associated protein that binds to a bioactive molecule (i.e., a ligand) and mediates the effect of the ligand on the cell. Membrane-bound receptors are characterized by a multi-domain structure comprising an extracellular ligand-binding domain and an intracellular effector domain that is typically involved in signal transduction.

By "multimeric" or "heteromultimeric" is meant comprising two or more different subunits. A "heterodimeric" receptor contains two different subunits, wherein a "heterotrimeric" molecule comprises three subunits.

By "soluble" multimeric receptor is meant herein a multimeric receptor, each of whose subunits comprises part or all of an extracellular domain of a receptor, but lacks part or all of any transmembrane domain, and lacks all of any intracellular domain. In general, a soluble receptor of the invention is soluble in an aqueous solution.

A "fusion" protein is a protein comprising two polypeptide segments linked by a peptide bond, produced, e.g., by recombinant processes.

As used herein, a "variant" polypeptide of a parent or wild-type polypeptide contains one or more amino acid substitutions, deletions and/or additions as compared to the parent or wild-type. Typically, such variants have a sequence identity to the parent or wild-type sequence of at least about 90%, at least about 95%, at least about 96%, at least about 97%, 98%, or at least about 99%, and have preserved or improved properties as compared to the parent or wild-type polypeptide. Some changes may not significantly affect the folding or activity of the protein or polypeptide; conservative amino acid substitutions, as are well known in the art, changing one amino acid to one having a side-chain with similar physicochemical properties (basic amino acid: arginine, lysine, and histidine; acidic amino acids: glutamic acid, and aspartic acid; polar amino acids: glutamine and asparagine; hydrophobic amino acids: leucine, isoleucine, valine; aromatic amino acids: phenylalanine, tryptophan, tyrosine; small amino acids: glycine, alanine, serine, threonine, methionine), small deletions, typically of one to about 30 amino acids; and small amino- or carboxyl-terminal extensions, such as an amino-terminal methionine residue, a small linker peptide of up to about 20-25 residues, or a small extension that facilitates purification (an affinity tag), such as a poly-histidine tract, protein A (Nilsson et al., EMBO 1985; 14:1075 et seq.; Nilsson et al., Methods Enzymol. 1991; 198:3 et seq.), glutathione S-transferase (Smith and Johnson, Gene 1988; 67:31 et seq.), or other antigenic:epitope or binding domain. See, in general Ford et al., Protein Expression and Purification 1991; 2:95-107. DNAs encoding affinity tags are available from commercial suppliers.

Sequence differences or "identity," in the context of amino acid sequences, can be determined by any suitable technique, such as (and as one suitable selection in the context of this invention) by employing a Needleman-Wunsch alignment analysis (see Needleman and Wunsch, J. Mol. Biol. (1970) 48:443453), such as is provided via analysis with ALIGN 2.0 using the BLOSUM50 scoring matrix with an initial gap penalty of −12 and an extension penalty of −2 (see Myers and Miller, CABIOS (1989) 4:11-17 for discussion of the global alignment techniques incorporated in the ALIGN program). A copy of the ALIGN 2.0 program is available, e.g., through the San Diego Supercomputer (SDSC) Biology Workbench. Because Needleman-Wunsch alignment provides an overall or global identity measurement between two sequences, it should be recognized that target sequences which may be portions or subsequences of larger peptide sequences may be used in a manner analogous to complete sequences or, alternatively, local alignment values can be used to assess relationships between subsequences, as determined by, e.g., a Smith-Waterman alignment (J. Mol. Biol. (1981) 147:195-197), which can be obtained through available programs (other local alignment methods that may be suitable for analyzing identity include programs that apply heuristic local alignment algorithms such as FastA and BLAST programs).

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel. Moreover, an "isolated nucleic acid fragment" or "isolated peptide" is a nucleic acid or protein fragment that is not naturally occurring as a fragment and/or is not typically in the functional state.

Moieties of the invention, such as polypeptides or peptides may be conjugated or linked covalently or noncovalently to other moieties such as polypeptides, proteins, peptides, supports, fluorescence moieties, or labels. The term "conjugate" is broadly used to define the operative association of one moiety with another agent and is not intended to refer solely to any type of operative association, and is particularly not limited to chemical "conjugation." Recombinant fusion proteins are particularly contemplated.

The term "providing" is used according to its ordinary meaning to indicate "to supply or furnish for use." In some embodiments, the protein is provided directly by administering the protein, while in other embodiments, the protein is effectively provided by administering a nucleic acid that encodes the protein. In certain aspects the invention contemplates compositions comprising various combinations of nucleic acid, antigens, peptides, and/or epitopes.

An effective amount means an amount of active ingredients necessary to treat, ameliorate, or mitigate a disease or a condition related to a disease. In more specific aspects, an effective amount prevents, alleviates, or ameliorates symptoms of disease, or prolongs the survival of the subject being treated, or improves the quality of life of an individual. Determination of the effective amount is well within the capability of those skilled in the art, especially in light of the detailed disclosure provided herein. For any preparation used in the methods of the invention, an effective amount or dose can be estimated initially from in vitro studies, cell culture, and/or animal model assays. For example, a dose can be formulated in animal models to achieve a desired response or circulating fusion protein concentration. Such information can be used to more accurately determine useful doses in humans.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

The mass normalized sensorgrams are shown in panels a and b; plots of the mass normalized equilibrium response ($R_{eq}$) as a function of receptor concentration ([Receptor]), along with fits to $R_{eg}=(R_{max}\times[Receptor])/(K_d+[Receptor])$, are shown in panel c.

FIG. 2. SPR sensorgrams in which increasing concentrations of the TGF-β type II receptor ectodomain were injected over immobilized TGF-β2 K25R I92V K94R in the absence (panel a) or presence (panel b) of a saturating concentration (800 nM) of the TGF-β type III receptor endoglin domain. Plots of the mass normalized equilibrium response ($R_{eq}$) as a function of receptor concentration ([Receptor]), along with fits to $R_{eq}=(R_{max}\times[Receptor])/(K_d+[Receptor])$, are shown in panel c.

Figure 3:
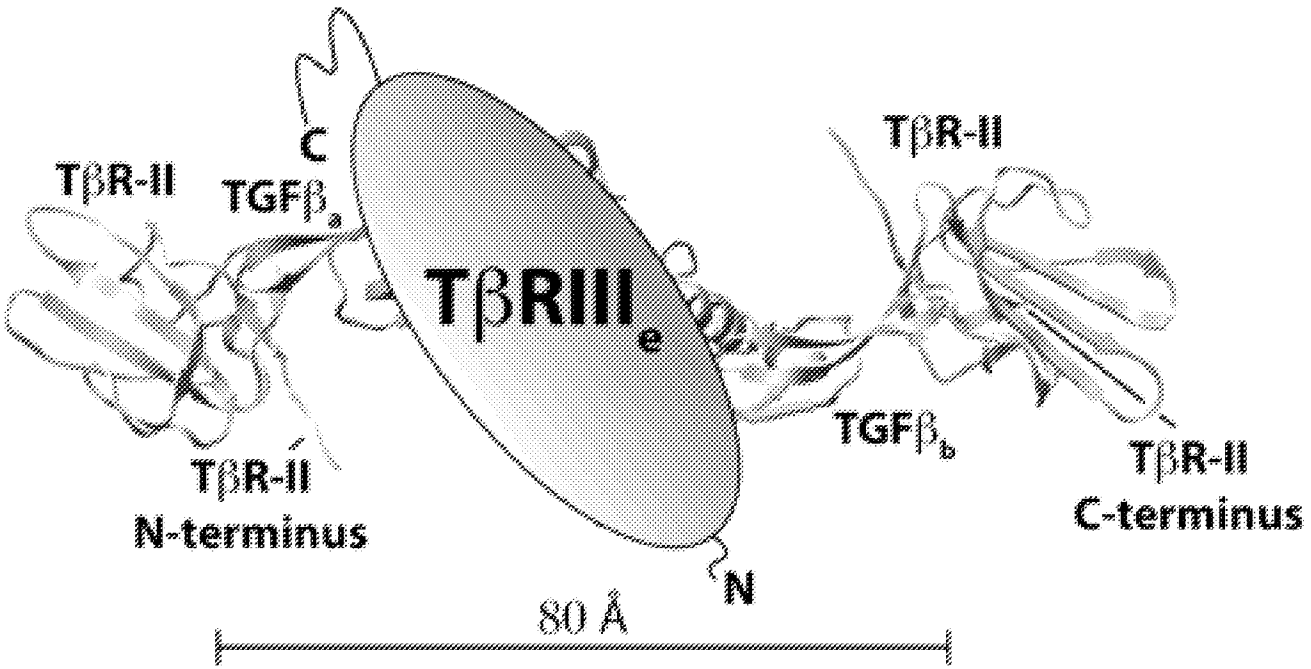

FIG. 3. Schematic diagram of the TGFβ:TβRII complex with the TGFβ type III receptor endoglin domain positioned in a manner that it does not sterically overlap with either of the two bound TβRII molecules. The locations on the TβRII N- and C-termini are shown.

Figure 4:
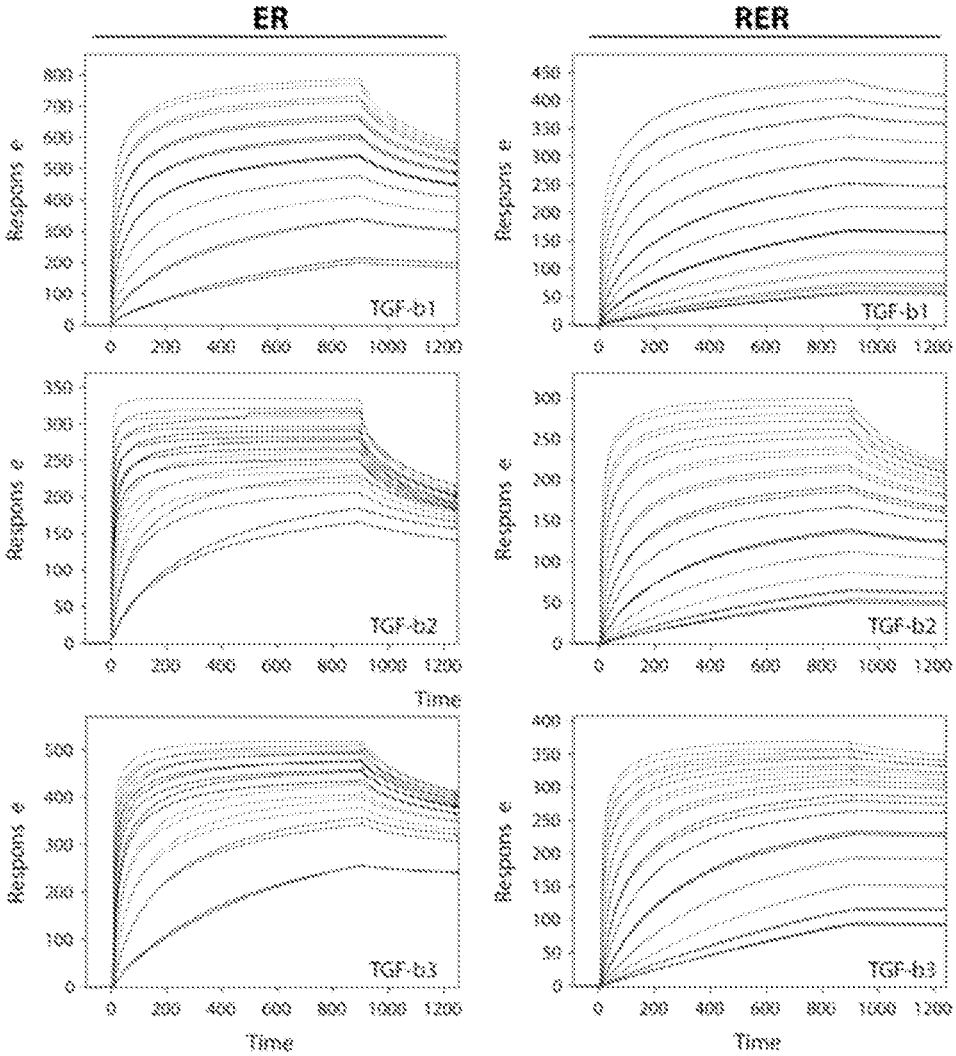

FIG. 4. SPR sensorgrams in which increasing concentrations of ER and RER were injected over SPR surfaces with immobilized TGF-β1, -β2, and -β3. The concentrations of injected receptor range from 10 nM downward (in two-fold increments).

Figure 5:
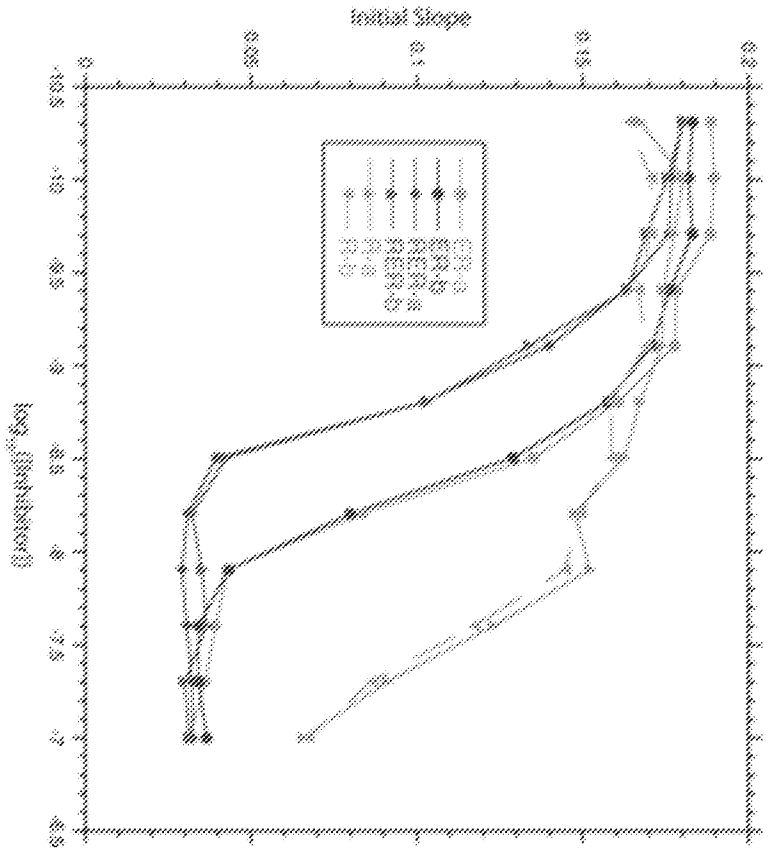

FIG. 5. SPR competition binding data in which increasing concentrations of TβRII (R), $T\beta RIII_E$-TβRII (ER), and TβRII-$T\beta RIII_E$-TβRII (RER) were pre-incubated with 0.8 nM TGF-β3 for 16 h and then injected over a high-density (20000 RU) SPR surface with the TGF-β monoclonal antibody 1D11. Data is presented in terms of the initial slope (which is directly proportional to the concentration of free TGF-β) as a function of the competitor (R, ER, or RER) concentration. Two independent measurements were performed for each of the receptor constructs studied (designated by the a and b suffices in the legend).

FIG. 6. Average $IC_{50}$ using Mv1Lu PAI1 luciferase reporter cells in 96-well plates. Assays were performed using a four-fold receptor fusion and 1D11 (neutralizing antibody) dilution series and 20 pM TGF-beta 1, 2, or 3 at 37° overnight.

Figure 7A:
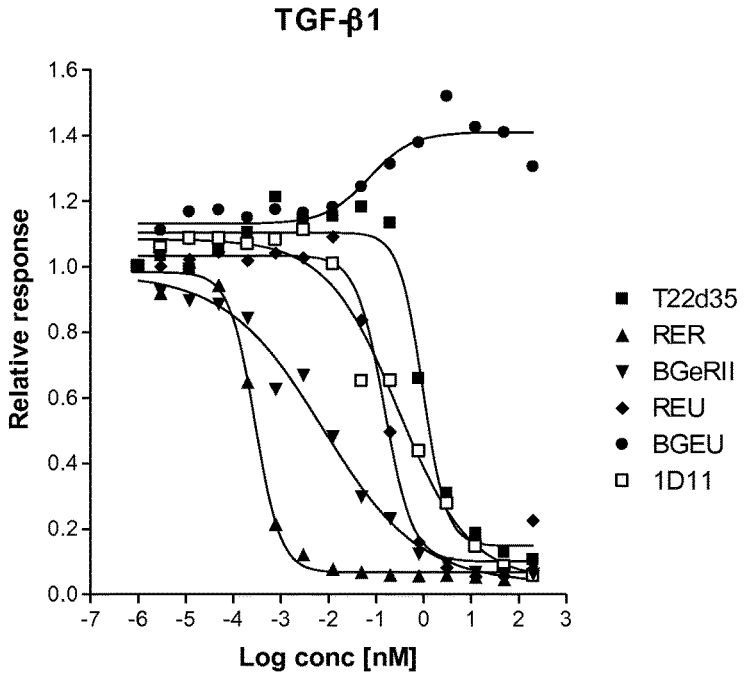
Figure 7B:
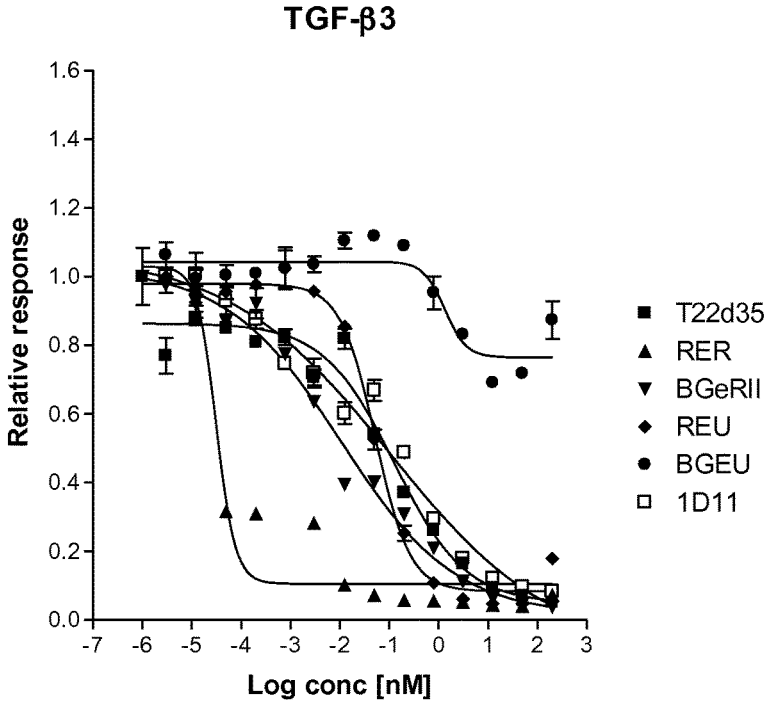
Figure 7C:
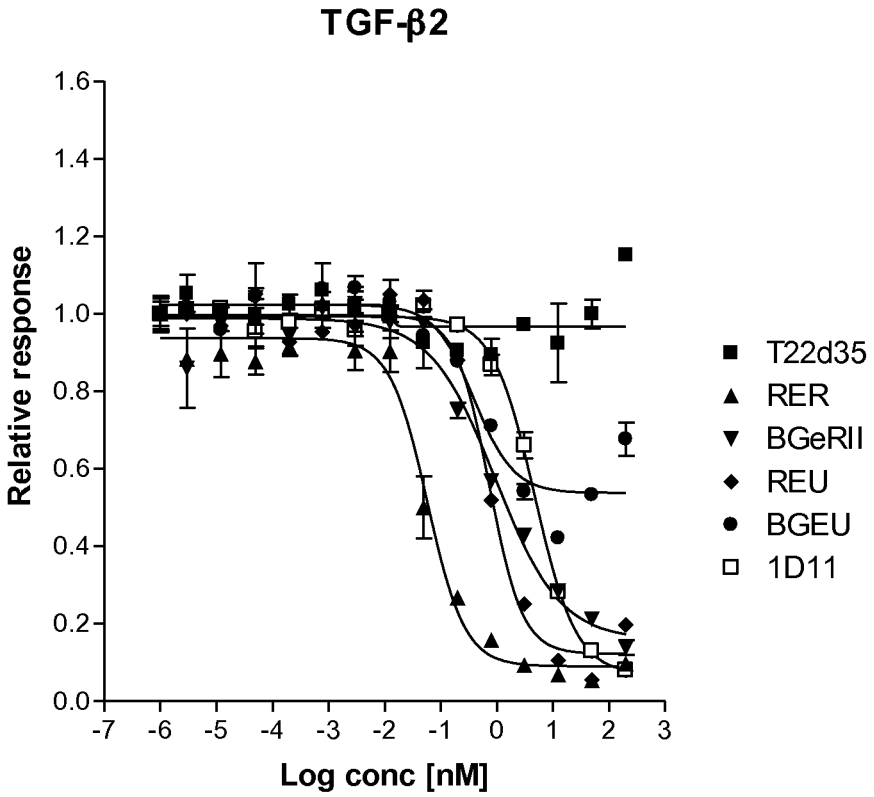

FIGS. 7A-7C. Neutralization curves comparing various traps (RR (RII-RII), RER (RII-$BG_E$-RII), ER ($BG_E$-RII), REU (RII-$BG_E$-$BG_U$, or alternatively RII-RIII), or EU ($BG_E$-$BG_U$, or alternatively RIII) and 1D11 for (A) TGF-β1, (B) TGF-β2, or TGF-β3.

Figure 8A:
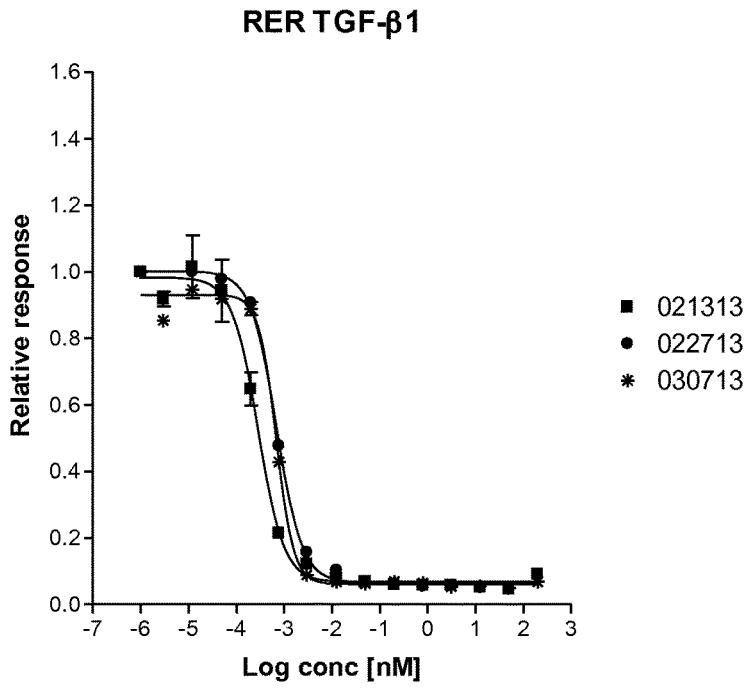
Figure 8B:
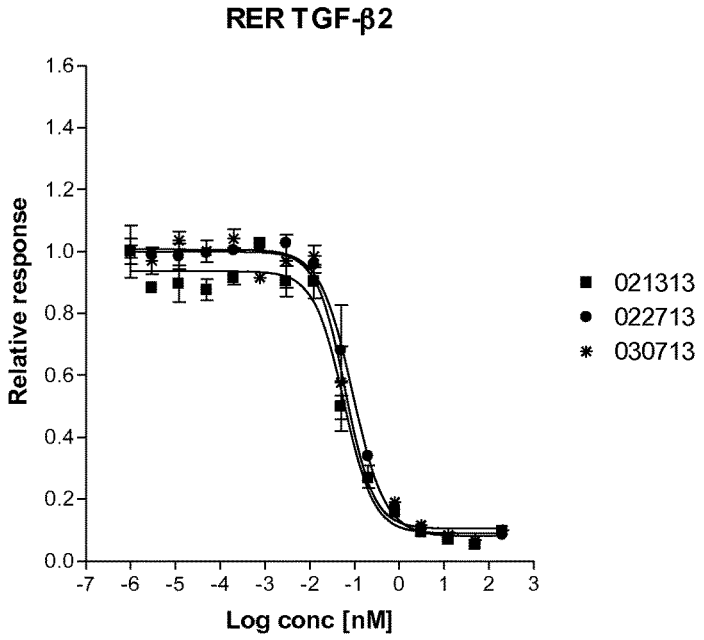
Figure 8C:
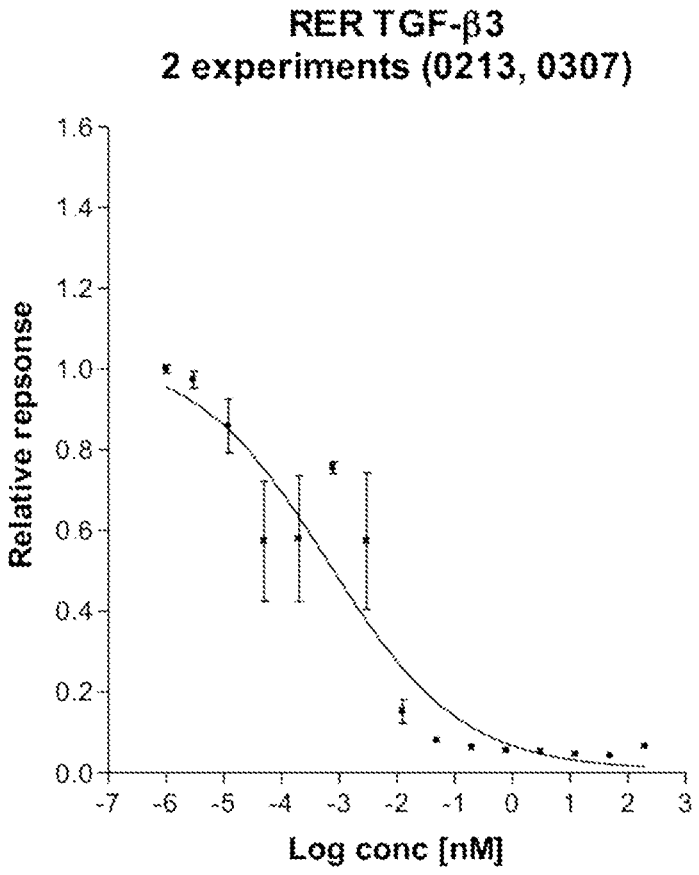

FIGS. 8A-8C. Neutralization curves for various RER preparations relative to (A) TGF-β1, (B) TGF-β2, or (c) TGF-β3

DESCRIPTION

As discussed above, transforming growth factor beta (TGFβ) isoforms (β1, β2, and β3) are homodimeric polypeptides of 25 kDa. TGF-β has nine cysteine residues that are conserved among its family; eight cysteines form four disulfide bonds within the molecule, three of which form a cystine knot structure characteristic of the TGF-β superfamily, while the ninth cysteine forms a disulfide bond with the ninth cysteine of another TGF-β molecule to produce the dimer.

Figures 1A, 1B, 1C:
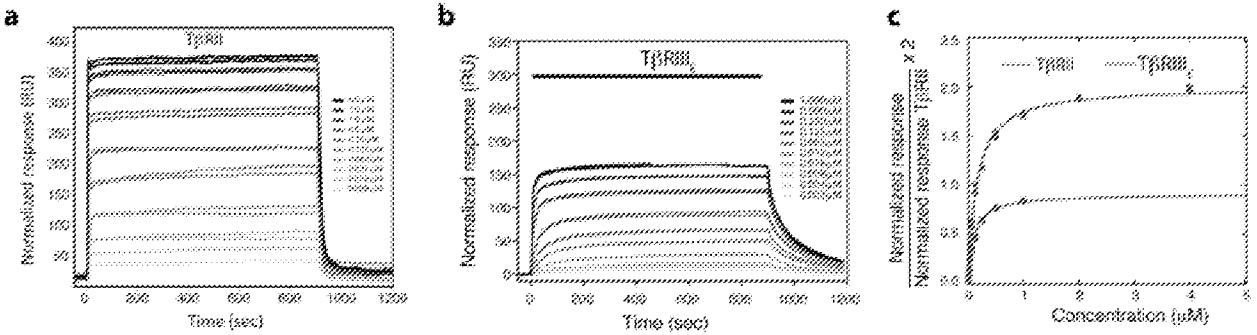
FIG. 1. SPR sensorgrams in which increasing concentrations of the TβRII and $T\beta RIII_E$ were injected over a SPR sensor surface with immobilized TGF-β2 K25R I92V K94R.

Though a number of TGF-β inhibitors have been reported, none have been approved for clinical use. The novel TGF-β inhibitor described herein—RER—can be produced by artificially fusing together the binding domains of the TGFβ type II receptor and the endoglin domain of the type III receptor. The design of RER—a heterotrimeric fusion in which the ectodomain of the TGF-β type II receptor (R) has been artificially fused onto the N- and C-termini of the endoglin-like domain of the TGF-β type III receptor (E)—was conceived based on the structures of the TGF-βs bound to the their signaling receptors, TβRI and TβRII, and the results of surface plasmon resonance (SPR) binding studies which showed that:

1. The TGF-β type III receptor endoglin domain binds TGF-β dimers with a stoichiometry of 1:1. This was shown by comparing the maximal mass-normalized SPR response as increasing concentrations of the purified TGF-β type II receptor ectodomain (TβRII or R) and purified TGF-β type III receptor endoglin-like domain ($T\beta RIII_E$ or E) were injected over immobilized TGF-β2 K25R I92V K94R, a variant of TGF-β2 that binds TβRII with high affinity (FIGS. 1A and 1B) (De Crescenzo et al. J Mol. Biol. 355, 47-62, 2006; Baardsnes et al. Biochemistry 48, 2146-55, 2009). The maximal mass-normalized response for $T\beta RIII_E$ was found to be approximately one-half of that for TORII, allowing the inventors to infer that $T\beta RIII_E$ must bind the TGF-β dimer with 1:1 stoichiometry since it is well established through structural studies that TβRII binds TGF-β dimers with 2:1 stoichiometry (FIG. 1C) (Hart et al., Nat Struct Biol. 9, 203-8, 2002; Groppe et al., Mol Cell 29, 157-68, 2008; Radaev et al., Journal of Biological Chemistry 285, 14806-14, 2010).

Figures 2A, 2B, 2C:
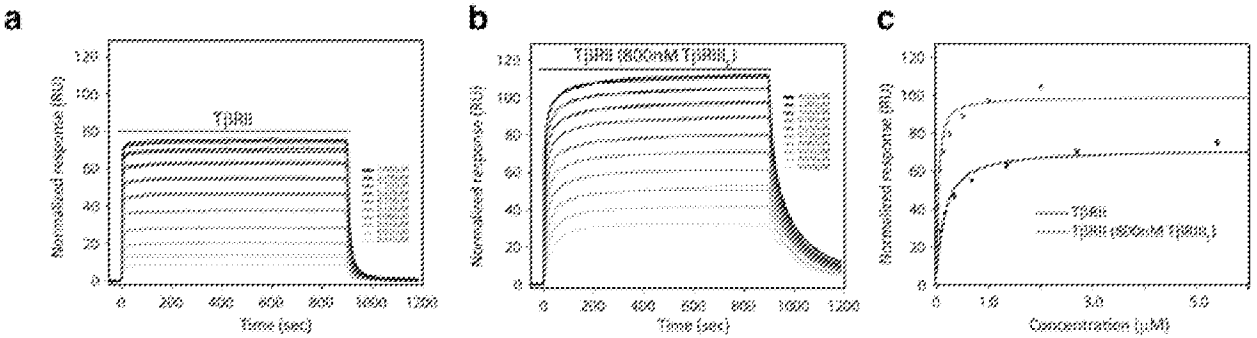

2. $T\beta RIII_E$ binds TGF-β dimers without displacing either of the two bound TβRIIs. This was shown by performing an SPR experiment in which increasing concentrations of TβRII were injected over immobilized TGF-β2 K25R I92V K94R in the absence or presence of a saturating concentration of $T\beta RIII_E$ (800 nM) (FIGS. 2A and 2B). The data showed that the maximal mass normalized binding response for TβRII was slightly increased in the presence of 800 nM $T\beta RIII_E$ (FIG. 2C), showing that the two receptors do not compete with one another for binding TGF-β (it is impossible for more than two TβRIIs to bind the TGF-β dimer, and thus the increase in the maximal amplitude is likely caused by an experimental artifact, such as a mismatch in the concentrations of $T\beta RIII_E$ in the TβRII samples that were injected and the buffer).

Together, these observations suggest that TGF-β dimers are capable of forming a heterotrimeric complex in which each TGF-β dimer binds two molecules of TβRII and one molecule of $T\beta RIII_E$. The structure of the TGF-β bound to TβRII has been reported (Hart et al., Nat Struct Biol. 9, 203-8, 2002; Groppe et al., Mol Cell 29, 157-68, 2008; Radaev et al., Journal of Biological Chemistry 285, 14806-14, 2010), but the structure of $T\beta RIII_E$, either alone or bound to TGF-β, has not. This has led to the hybrid structure where the precise structure of $T\beta RIII_E$ is not known, but its overall positioning between the two bound TβRIIs on the distal ends of the TGF-β dimer is known (FIG. 3).

This hybrid model for binding of TβRII and $T\beta RIII_E$ led to the construction of the heterotrimeric RER (TβRII-$T\beta RIII_E$-TβRII) fusion as a novel inhibitor for binding and sequestering TGF-β. The inclusion of an additional binding domain enhanced the affinity of the fusion for the TGF-βs, especially TGF-β1 and TGF-β3, which bind TβRII with high ($K_d$ ~120 nM) affinity (Baardsnes et al. Biochemistry 48, 2146-55, 2009; Radaev et al., Journal of Biological Chemistry 285, 14806-14, 2010).

In comparison to the currently described RER, Genzyme's monoclonal antibody GC1008 (the humanized version of the mouse monoclonal antibody 1D11) has been shown to bind the three TGF-β isoforms with a $K_d$ of approximately 5-10 nM (Grütter, et. al., PNAS U.S.A. 105(51): 20251-56, 2008), but it has not proven to be very effective in clinical trials for malignant melanoma and renal cell carcinoma. The reason for the lack of effectiveness might be that GC1008 does not bind the TGF-βs tightly enough to compete against the cell surface TGF-β receptors, which bind the TGF-βs at picomolar to sub-picomolar concentrations.

The polypeptides described herein include high affinity heterotrimeric TGF-β inhibitors, such as RER. As described above RER has been shown to bind all three TGF-β isoforms with low nanomolar affinity to sub-nanomolar affinity. RER is more potent than the monoclonal antibody 1D11. Thus, owing to its enhanced affinity for binding TGF-β, RER more effectively competes against the cell surface receptors for binding TGF-β, and in turn blocking its disease-promoting properties in cancer and fibrosis for example.

An example of an RER amino acid sequence (for example see SEQ ID NO:2) has one or more of the following features:

1. In certain aspects the TβRII sequence is human (SEQ ID NO:6), while the $T\beta RIII_E$ sequence can be rat (SEQ ID NO:7). In certain aspects the $T\beta RIII_E$ sequence can be human (SEQ ID NO:8).

2. In certain embodiments the N-terminal TβRII sequence of RER extends from residue 42-160 of SEQ ID NO:6, while the C-terminal TβRII sequence of RER extends from residue 48-160 of SEQ ID NO:6.

3. In certain embodiments the $T\beta RIII_E$ sequence extends from residue 24-383 of SEQ ID NO:7. In certain aspects, the $T\beta RIII_E$ sequence includes 1, 2, 3, and/or 4 single amino acid substitutions relative to the wild type rat sequence (SEQ ID NO:7), R58H, H116R, C278S, and N337A.

4. In certain embodiments there is no linker between $T\beta RIII_E$ and the C-terminal TβRII domain. In other aspects a Lys-Leu dipeptide encoded by the HindIII restriction site used to join the corresponding DNA fragments together forms a linker. It is contemplated that any dipeptide can be used.

5. In certain embodiments there is an 18 amino acid linker with the sequence Gly-Leu-Gly-Pro-Val-Glu-Ser-Ser-Pro-Gly-His-Gly-Leu-Asp-Thr-Ala-Ala-Ala (SEQ ID NO:9) that links the C-terminus of the N-terminal TβRII to the N-terminus of $T\beta RIII_E$.

6. In certain embodiments there is a C-terminal hexa-histidine tag (for purification purposes).

In one example, an RER expression cassette was inserted downstream of the albumin signal peptide and an engineered NotI cloning site with the sequence Met-Lys-Trp-Val-Thr-Phe-Leu-Leu-Leu-Leu-Phe-Ile-Ser-Gly-Ser-Ala-Phe-Ser-Ala-Ala-Ala (SEQ ID NO:10). The entire albumin signal peptide was placed downstream of the CMV promoter in a modified form of pcDNA3.1 (Invitrogen) as previously described (Zou and Sun, Cell 134, 215-30, 2004).

A plasmid expressing RER construct was transfected into CHO Lec 3.2.8.1 cells (Rosenwald et al., Mol Cell Biol. 9(3):914-24, 1989) and stable transfectants were selected using MSX (Zou and Sun, Cell 134, 215-30, 2004). The stable transfectants were in turn screened for high level expression of the RER fusion by examining the conditioned medium using a polyclonal antibody raised against the rat betaglycan ectodomain. The clone expressing RER at the highest level was expanded and ultimately transferred into serum free medium for production of conditioned medium. The RER was then purified from the conditioned medium by passing it over a NiNTA column, washing it with 25 mM Tris, 100 mM NaCl, and 10 mM imidazole, pH 8 and ultimately by eluting it with the same buffer, but with 300 mM imidazole.

The isolated RER fusion protein was in turn characterized by performing an SPR experiment in which it, together with similarly prepared ER (i.e. the previously described $T\beta RIII_E T\beta RII$ fusion (Verona et al., Protein Eng Des Sel. 21, 463-73, 2008), except produced in CHO cells, not bacteria), was injected over a SPR sensor chip with immobilized TGF-β1, -β2, and -β3. This data showed comparable on-rates, but significantly slower off-rates, especially for TGF-β1 and TGF-β3 (FIG. 4). This qualitatively shows that RER binds the TGF-βs with higher affinity than ER; however, the magnitude of this increase proved to be difficult to quantify since the slow association precluded accurate measurement of the equilibrium SPR response, especially at lower concentrations of injected receptor.

To further evaluate affinity, an SPR competition experiment was performed in which the commercially available TGF-β monoclonal antibody 1D11 (R&D Systems) was coupled to an SPR sensor chip at high density (20000 RU) and in turn increasing concentration of R (TβRII), ER ($BG_E$-RII), or RER(RII-$BG_E$-RII) were injected in the presence of a fixed low (0.8 nM) concentration of TGF-β3. The initial slope of these sensorgrams (which is a linear function of the free TGF-β3 concentration) was then plotted as a function of the concentration of the receptor fusion (FIG. 5). This showed that RER is indeed a more potent competitor than ER, consistent with the slower dissociation rate for RER compared to ER.

RER polypeptides demonstrate more potent activity relative to similar fusion proteins. For example the average $IC_{50}$ [nM] using Mv1Lu PAI1 luciferase reporter cells in 96-well plates is markedly lower for RER polypeptides (FIG. 6). Neutralization curves comparing various receptor fusions (RR (RII-RII, also known as T22d35), RER (RII-$BG_E$-RII), ER ($BG_E$-RII), REU (RII-$BG_E$-$BG_U$ or alternatively RII-RIII), or EU ($BG_E$-$BG_U$ or alternatively RIII) and 1D11 for (A) TGF-β1, (B) TGF-β2, or TGF-β3 also show an improved activity for RER polypeptides (FIG. 7 and FIG. 8).

I. Linkers

In some embodiments, the invention provides a fusion protein comprising three TGF-β binding domains joined to each other directly or by a linker, such as, e.g., a short peptide linker. In some embodiments, the C terminus of the amino terminal TGF-β binding segment is joined by a peptide linker to the N terminus of the central TGF-β binding segment, and the C terminus of the center TGFβ binding segment may be joined to the N terminus of the carboxy TGFβ binding segment by a second linker. A linker is considered short if it contains 2, 3, 4, 5, 6, 7, 8, 9, 10, 11, 12, 13, 14, 15, 16, 17, 18, 19, 20, 25, to 50 or fewer amino acids.

Most typically, the linker is a peptide linker that contains 50 or fewer amino acids, e.g., 45, 40, 35, 30, 25, 20, 15, 10, 9, 8, 7, 6, 5, 3, 4, 2, or 1 amino acid(s). In certain aspects, the sequence of the peptide linker is a non-TGF-β type II or type III receptor amino acid sequence. In other aspects, the sequence of the peptide linker is additional TGF-β type II or type III receptor amino acid sequence, e.g., the 2, 3, 4, 5, 6, 7, 8, 9, 10, 11, 12, 13, 14, 15, 16, 17, 18, 19, 20, 25, to 50 or fewer amino acids flanking the carboxy an/or amino terminal ends of the binding domains. The term additional in this context refers to amino acids in addition to those that define the segments of the heterotrimeric polypeptide as defined above. In various embodiments, the linker does not contain more than 50, 40, 20, 10, or 5 contiguous amino acids from the native receptor sequences. Typically, the linker will be flexible and allow the proper folding of the joined domains. Amino acids that do not have bulky side groups and charged groups are generally preferred (e.g., glycine, serine, alanine, and threonine). Optionally, the linker may additionally contain one or more adaptor amino acids, such as, for example, those produced as a result of the insertion of restriction sites. Generally, there will be no more than 10, 9, 8, 7, 6, 5, 4, 3, 2 adaptor amino acids in a linker.

In some embodiments, the linker comprises one or more glycines, e.g., 1, 2, 3, 4, 5, 6, 7, 8, 9, 10, 11, 12, 15, 18, or more glycines. For example, the linker may consist of (GGG)n, where n=1, 2, 3, 4, 5, 6, 7, etc. and optional adaptor amino acids. In certain aspects, the linker is a glycine-serine linker which comprises (GGGS)n, where n=1, 2, 3, 4, 5, etc. In view of the results disclosed herein, the skilled artisan will recognize that any other suitable peptide linker can be used in the fusion proteins of the invention, for example, as described in Alfthan et al., Protein Eng. 8:725-31, 1995; Argos, J. MoI. Biol. 211:943-58, 1990; Crasto et al., Protein Eng., 13:309-12, 2000; Robinson et al., PNAS USA, 95:5929-34, 1998.

II. Nucleic Acids, Vectors, Host Cells

The invention further provides nucleic acids encoding any of the fusion proteins of the invention, vectors comprising such nucleic acids, and host cells comprising such nucleic acids. For example, in an illustrative embodiment, the nucleic acid of the invention comprises the sequence as set forth in SEQ ID NO:1.

Nucleic acids of the invention can be incorporated into a vector, e.g., an expression vector, using standard techniques. The expression vector may then be introduced into host cells using a variety of standard techniques such as liposome-mediated transfection, calcium phosphate precipitation, or electroporation. The host cells according to the present invention can be mammalian cells, for example, Chinese hamster ovary cells, human embryonic kidney cells (e.g., HEK 293), HeLa S3 cells, murine embryonic cells, or NSO cells. However, non-mammalian cells can also be used, including, e.g., bacteria, yeast, insect, and plant cells. Suitable host cells may also reside in vivo or be implanted in vivo, in which case the nucleic acids could be used in the context of in vivo or ex vivo gene therapy.

III. Methods of Making

The invention also provides methods of producing (a) fusion proteins, (b) nucleic acid encoding the same, and (c) host cells and pharmaceutical compositions comprising either the fusion proteins or nucleic acids. For example, a method of producing the fusion protein according to the invention comprises culturing a host cell, containing a nucleic acid that encodes the fusion protein of the invention under conditions resulting in the expression of the fusion protein and subsequent recovery of the fusion protein. In one aspect, the fusion protein is expressed in CHO or HEK 293 cells and purified from the medium using methods known in the art. In some embodiments, the fusion protein is eluted from a column at a neutral pH or above, e.g., pH 7.5 or above, pH 8.0 or above, pH 8.5 or above, or pH 9.0 or above.

The fusion proteins, including variants, as well as nucleic acids encoding the same, can be made using any suitable method, including standard molecular biology techniques and synthetic methods, for example, as described in the following references: Maniatis (1990) Molecular Cloning, A Laboratory Manual, 2nd ed., Cold Spring Harbor Laboratory, Cold Spring Harbor, N.Y., and Bodansky et al. (1995) The Practice of Peptide Synthesis, 2nd ed., Spring Verlag, Berlin, Germany). Pharmaceutical compositions can also be made using any suitable method, including for example, as described in Remington: The Science and Practice of Pharmacy, eds. Gennado et al., 21th ed., Lippincott, Williams & Wilkins, 2005).

IV. Pharmaceutical Compositions and Methods of Administration

The invention provides pharmaceutical compositions comprising the fusion proteins of the invention or nucleic acids encoding the fusion proteins.

The fusion protein may be delivered to a cell or organism by means of gene therapy, wherein a nucleic acid sequence encoding the fusion protein is inserted into an expression vector that is administered in vivo or to cells ex vivo, which are then administered in vivo, and the fusion protein is expressed therefrom. Methods for gene therapy to deliver TGF-β antagonists are known (see, e.g., Fakhrai et al., PNAS USA, 93:2909-14, 1996 and U.S. Pat. No. 5,824,655).

The fusion protein may be administered to a cell or organism in a pharmaceutical composition that comprises the fusion protein as an active ingredient. Pharmaceutical compositions can be formulated depending upon the treatment being effected and the route of administration. For example, pharmaceutical compositions of the invention can be administered orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes. The pharmaceutical composition will typically comprise biologically inactive components, such as diluents, excipients, salts, buffers, preservants, etc. Standard pharmaceutical formulation techniques and excipients are well known to persons skilled in the art (see, e.g., Physicians' Desk Reference (PDR) 2005, 59th ed., Medical Economics Company, 2004; and Remington: The Science and Practice of Pharmacy, eds. Gennado et al. 21th ed., Lippincott, Williams & Wilkins, 2005).

Generally, the fusion protein of the invention may be administered as a dose of approximately from 1 μg/kg to 25 mg/kg, depending on the severity of the symptoms and the progression of the disease. The appropriate therapeutically effective dose of an antagonist is selected by a treating clinician and would range approximately from 1 μg/kg to 20 mg/kg, from 1 μg/kg to 10 mg/kg, from 1 μg/kg to 1 mg/kg, from 10 μg/kg to 1 mg/kg, from 10 μg/kg to 100 μg/kg, from 100 μg to 1 mg/kg, and from 500 μg/kg to 5 mg/kg. Effective dosages achieved in one animal may be converted for use in another animal, including human, using conversion factors known in the art (see, e.g., Freireich et al., Cancer Chemother. Reports, 50(4):219-244 (1996)).

V. Therapeutic and Non-Therapeutic Uses

The fusion proteins of the invention may be used to capture or neutralize TGF-β, thus reducing or preventing TGF-β binding to naturally occurring TGF-β receptors.

The invention includes a method of treating a subject (e.g., mammal) by administering to the mammal a fusion protein described herein or a nucleic acid encoding the fusion protein or cells containing a nucleic acid encoding the fusion protein. The mammal can be for example, primate (e.g., human), rodent (e.g., mouse, guinea pig, rat), or others (such as, e.g., dog, pig, rabbit).

The mammal being treated may have or may be at risk for one or more conditions associated with an excess of TGF-β for which a reduction in TGF-β levels may be desirable. Such conditions include, but are not limited to, fibrotic diseases (such as glomerulonephritis, neural scarring, dermal scarring, pulmonary fibrosis (e.g., idiopathic pulmonary fibrosis), lung fibrosis, radiation-induced fibrosis, hepatic fibrosis, myelofibrosis), peritoneal adhesions, hyperproliferative diseases (e.g., cancer), burns, immune-mediated diseases, inflammatory diseases (including rheumatoid arthritis), transplant rejection, Dupuytren's contracture, and gastric ulcers.

In certain embodiments, the fusion proteins, nucleic acids, and cells of the invention are used to treat diseases and conditions associated with the deposition of extracellular matrix (ECM). Such diseases and conditions include, but are not limited to, systemic sclerosis, postoperative adhesions, keloid and hypertrophic scarring, proliferative vitreoretinopathy, glaucoma drainage surgery, corneal injury, cataract, Peyronie's disease, adult respiratory distress syndrome, cirrhosis of the liver, post myocardial infarction scarring, restenosis (e.g., post-angioplasty restenosis), scarring after subarachnoid hemorrahage, multiple sclerosis, fibrosis after laminectomy, fibrosis after tendon and other repairs, scarring due to tatoo removal, biliary cirrhosis (including sclerosing cholangitis), pericarditis, pleurisy, tracheostomy, penetrating CNS injury, eosinophilic myalgic syndrome, vascular restenosis, veno-occlusive disease, pancreatitis and psoriatic arthropathy. In particular, the fusion proteins, and related aspects of the invention are particularly useful for the treatment of peritoneal fibrosis/adhesions. It is well known that antibodies are readily transferred from the peritoneal cavity into circulation. Therefore, intraperitoneal delivery of the fusion protein may provide a highly localized form of treatment for peritoneal disorders like peritoneal fibrosis and adhesions due to the advantageous concentration of the fusion protein within the affected peritoneum.

The fusion proteins, nucleic acids, and cells of the invention are also useful to treat conditions where promotion of re-epithelialization is beneficial. Such conditions include, but are not limited to: diseases of the skin, such as venous ulcers, ischaemic ulcers (pressure sores), diabetic ulcers, graft sites, graft donor sites, abrasions and burns; diseases of the bronchial epithelium, such as asthma and ARDS; diseases of the intestinal epithelium, such as mucositis associated with cytotoxic treatment, esophagial ulcers (reflex disease), stomach ulcers, and small intestinal and large intestinal lesions (inflammatory bowel disease).

Still further uses of the fusion proteins, nucleic acids, and cells of the invention are in conditions in which endothelial cell proliferation is desirable, for example, in stabilizing atherosclerotic plaques, promoting healing of vascular anastomoses, or in conditions in which inhibition of smooth muscle cell proliferation is desirable, such as in arterial disease, restenosis and asthma.

The fusion proteins, nucleic acids, and cells of the invention are also useful in the treatment of hyperproliferative diseases, such as cancers including, but not limited to, breast, prostate, ovarian, stomach, renal (e.g., renal cell carcinoma), pancreatic, colorectal, skin, lung, thyroid, cervical and bladder cancers, glioma, glioblastoma, mesothelioma, melanoma, as well as various leukemias and sarcomas, such as Kaposi's Sarcoma, and in particular are useful to treat or prevent recurrences or metastases of such tumors. In particular embodiments, the fusion proteins, nucleic acids, and cells of the invention are useful in methods of inhibiting cyclosporin-mediated metastases. It will of course be appreciated that in the context of cancer therapy, "treatment" includes any medical intervention resulting in the slowing of tumor growth or reduction in tumor metastases, as well as partial remission of the cancer in order to prolong life expectancy of a patient. In one embodiment, the invention is a method of treating cancer comprising administering a fusion protein, nucleic acid or cells of the invention. In particular embodiments, the condition is renal cancer, prostate cancer or melanoma.

The fusion proteins, nucleic acids, and cells of the invention are also useful for treating, preventing and reducing the risk of occurrence of renal insufficiencies including, but not limited to, diabetic (type I and type II) nephropathy, radiational nephropathy, obstructive nephropathy, diffuse systemic sclerosis, pulmonary fibrosis, allograft rejection, hereditary renal disease (e.g., polycystic kidney disease, medullary sponge kidney, horseshoe kidney), nephritis, glomerulonephritis, nephrosclerosis, nephrocalcinosis, systemic lupus erythematosus, Sjogren's syndrome, Berger's disease, systemic or glomerular hypertension, tubulointerstitial nephropathy, renal tubular acidosis, renal tuberculosis, and renal infarction. In particular embodiments, the fusion proteins, nucleic acids and cells of the invention are combined with antagonists of the renin-angiotensin-aldosterone system including, but not limited to, renin inhibitors, angiotensin-converting enzyme (ACE) inhibitors, Ang Ii receptor antagonists (also known as "Ang Il receptor blockers"), and aldosterone antagonists (see, for example, WO 2004/098637).

The fusion proteins, nucleic acids, and cells of the invention are also useful to enhance the immune response to macrophage-mediated infections, such as those caused by Leishmania spp., Trypanosoma cruzi, Mycobacterium tuberculosis and Mycobacterium leprae, as well as the protozoan Toxoplasma gondii, the fungi Histoplasma capsulatum, Candida albicans, Candida parapsilosis, and Cryptococcus neoformans, and Rickettsia, for example, R. prowazekii, R. coronii, and R. tsutsugamushi. They are also useful to reduce immunosuppression caused, for example, by tumors, AIDS or granulomatous diseases.

In addition, without being bound to any particular theory, it is also believed that the fusion proteins of the invention, because they lack an immunoglobulin domain (unlike TGF-β antibodies and TGF-β receptor-Fc fusion proteins) may not be as susceptible to clearance from sites of action by the immune system (e.g., in conditions or diseases of the lung).

SEQUENCE LISTING

```
<160> NUMBER OF SEQ ID NOS: 10

<210> SEQ ID NO 1
<211> LENGTH: 1893
<212> TYPE: DNA
<213> ORGANISM: Artificial Sequence
<220> FEATURE:
<223> OTHER INFORMATION: Synthetic polypeptide
<220> FEATURE:
<221> NAME/KEY: CDS
```

<222> LOCATION: (1)..(1893)

<400> SEQUENCE: 1

```
atg aag tgg gta acc ttt ctc ctc ctc ctc ttc atc tcc ggt tct gcc       48
Met Lys Trp Val Thr Phe Leu Leu Leu Leu Phe Ile Ser Gly Ser Ala
1               5                   10                  15

ttt tct gcg gcc gct aac ggt gca gtc aag ttt cca caa ctg tgt aaa       96
Phe Ser Ala Ala Ala Asn Gly Ala Val Lys Phe Pro Gln Leu Cys Lys
            20                  25                  30

ttt tgt gat gtg aga ttt tcc acc tgt gac aac cag aaa tcc tgc atg      144
Phe Cys Asp Val Arg Phe Ser Thr Cys Asp Asn Gln Lys Ser Cys Met
        35                  40                  45

agc aac tgc agc atc acc tcc atc tgt gag aag cca cag gaa gtc tgt      192
Ser Asn Cys Ser Ile Thr Ser Ile Cys Glu Lys Pro Gln Glu Val Cys
    50                  55                  60

gtg gct gta tgg aga aag aat gac gag aac ata aca cta gag aca gtt      240
Val Ala Val Trp Arg Lys Asn Asp Glu Asn Ile Thr Leu Glu Thr Val
65                  70                  75                  80

tgc cat gac ccc aag ctc ccc tac cat gac ttt att ctg gaa gat gct      288
Cys His Asp Pro Lys Leu Pro Tyr His Asp Phe Ile Leu Glu Asp Ala
                85                  90                  95

gct tct cca aag tgc att atg aag gaa aaa aaa aag cct ggt gag act      336
Ala Ser Pro Lys Cys Ile Met Lys Glu Lys Lys Lys Pro Gly Glu Thr
            100                 105                 110

ttc ttc atg tgt tcc tgt agc tct gat gag tgc aat gac aac atc atc      384
Phe Phe Met Cys Ser Cys Ser Ser Asp Glu Cys Asn Asp Asn Ile Ile
        115                 120                 125

ttc tca gaa gaa tat aac acc agc aat cct gac ggc ctt ggt cct gtg      432
Phe Ser Glu Glu Tyr Asn Thr Ser Asn Pro Asp Gly Leu Gly Pro Val
    130                 135                 140

gaa tca tca cct ggc cat ggc ctg gac acg gcg gcc gct ggt cca gag      480
Glu Ser Ser Pro Gly His Gly Leu Asp Thr Ala Ala Ala Gly Pro Glu
145                 150                 155                 160

ccc agc acc cgg tgt gaa ctg tca cca atc aac gcc tct cac cca gtc      528
Pro Ser Thr Arg Cys Glu Leu Ser Pro Ile Asn Ala Ser His Pro Val
                165                 170                 175

cag gcc ttg atg gag agc ttc acc gtt ctg tct ggc tgt gcc agc cat      576
Gln Ala Leu Met Glu Ser Phe Thr Val Leu Ser Gly Cys Ala Ser His
            180                 185                 190

ggc acc acc ggg ctg cca agg gag gtc cat gtc cta aac ctc cga agt      624
Gly Thr Thr Gly Leu Pro Arg Glu Val His Val Leu Asn Leu Arg Ser
        195                 200                 205

aca gat cag gga cca ggc cag cgg cag aga gag gtt acc ctg cac ctg      672
Thr Asp Gln Gly Pro Gly Gln Arg Gln Arg Glu Val Thr Leu His Leu
    210                 215                 220

aac ccc att gcc tcg gtg cac act cac cac aaa ccc atc gtg ttc ctg      720
Asn Pro Ile Ala Ser Val His Thr His His Lys Pro Ile Val Phe Leu
225                 230                 235                 240

ctc aac tcc ccc cag ccc ctg gtg tgg cgt ctg aag acg gag aga ctg      768
Leu Asn Ser Pro Gln Pro Leu Val Trp Arg Leu Lys Thr Glu Arg Leu
                245                 250                 255

gcc gct ggt gtc ccc aga ctc ttc ctg gtt tca gag ggt tct gtg gtc      816
Ala Ala Gly Val Pro Arg Leu Phe Leu Val Ser Glu Gly Ser Val Val
            260                 265                 270

cag ttt cca tca gga aac ttc tcc ttg aca gca gaa aca gag gaa agg      864
Gln Phe Pro Ser Gly Asn Phe Ser Leu Thr Ala Glu Thr Glu Glu Arg
        275                 280                 285

aat ttc cct caa gaa aat gaa cat ctg ctg cgc tgg gcc caa aag gaa      912
Asn Phe Pro Gln Glu Asn Glu His Leu Leu Arg Trp Ala Gln Lys Glu
    290                 295                 300
```

```
tat gga gca gtg act tcg ttc acc gaa ctc aag ata gca aga aac atc      960
Tyr Gly Ala Val Thr Ser Phe Thr Glu Leu Lys Ile Ala Arg Asn Ile
305                 310                 315                 320

tat att aaa gtg gga gaa gat caa gtg ttt cct cct acg tgt aac ata     1008
Tyr Ile Lys Val Gly Glu Asp Gln Val Phe Pro Pro Thr Cys Asn Ile
                325                 330                 335

ggg aag aat ttc ctc tca ctc aat tac ctt gcc gag tac ctt caa ccc     1056
Gly Lys Asn Phe Leu Ser Leu Asn Tyr Leu Ala Glu Tyr Leu Gln Pro
            340                 345                 350

aaa gcc gcc gaa ggt tgt gtc ctg ccc agt caa ccc cat gaa aag gaa     1104
Lys Ala Ala Glu Gly Cys Val Leu Pro Ser Gln Pro His Glu Lys Glu
        355                 360                 365

gta cac atc atc gag tta att acc ccc agc tcg aac cct tac agc gct     1152
Val His Ile Ile Glu Leu Ile Thr Pro Ser Ser Asn Pro Tyr Ser Ala
    370                 375                 380

ttc cag gtg gat ata ata gtt gac ata cga cct gct caa gag gat ccc     1200
Phe Gln Val Asp Ile Ile Val Asp Ile Arg Pro Ala Gln Glu Asp Pro
385                 390                 395                 400

gag gtg gtc aaa aac ctt gtc ctg atc ttg aag tcc aaa aag tct gtc     1248
Glu Val Val Lys Asn Leu Val Leu Ile Leu Lys Ser Lys Lys Ser Val
                405                 410                 415

aac tgg gtg atc aag tct ttt gac gtc aag gga aac ttg aaa gtc att     1296
Asn Trp Val Ile Lys Ser Phe Asp Val Lys Gly Asn Leu Lys Val Ile
            420                 425                 430

gct ccc aac agt atc ggc ttt gga aaa gag agt gaa cga tcc atg aca     1344
Ala Pro Asn Ser Ile Gly Phe Gly Lys Glu Ser Glu Arg Ser Met Thr
        435                 440                 445

atg acc aaa ttg gta aga gat gac atc cct tcc acc caa gag aat ctg     1392
Met Thr Lys Leu Val Arg Asp Asp Ile Pro Ser Thr Gln Glu Asn Leu
    450                 455                 460

atg aag tgg gca ctg gac gct ggc tac agg cca gtg acg tca tac aca     1440
Met Lys Trp Ala Leu Asp Ala Gly Tyr Arg Pro Val Thr Ser Tyr Thr
465                 470                 475                 480

atg gct ccc gtg gct aat aga ttt cat ctt cgg ctt gag aac aac gag     1488
Met Ala Pro Val Ala Asn Arg Phe His Leu Arg Leu Glu Asn Asn Glu
                485                 490                 495

gag atg aga gat gag gaa gtc cac acc att cct cct gag ctt cgt atc     1536
Glu Met Arg Asp Glu Glu Val His Thr Ile Pro Pro Glu Leu Arg Ile
            500                 505                 510

ctg ctg gac cct gac aag ctt cca caa ctg tgt aaa ttt tgt gat gtg     1584
Leu Leu Asp Pro Asp Lys Leu Pro Gln Leu Cys Lys Phe Cys Asp Val
        515                 520                 525

aga ttt tcc acc tgt gac aac cag aaa tcc tgc atg agc aac tgc agc     1632
Arg Phe Ser Thr Cys Asp Asn Gln Lys Ser Cys Met Ser Asn Cys Ser
    530                 535                 540

atc acc tcc atc tgt gag aag cca cag gaa gtc tgt gtg gct gta tgg     1680
Ile Thr Ser Ile Cys Glu Lys Pro Gln Glu Val Cys Val Ala Val Trp
545                 550                 555                 560

aga aag aat gac gag aac ata aca cta gag aca gtt tgc cat gac ccc     1728
Arg Lys Asn Asp Glu Asn Ile Thr Leu Glu Thr Val Cys His Asp Pro
                565                 570                 575

aag ctc ccc tac cat gac ttt att ctg gaa gat gct gct tct cca aag     1776
Lys Leu Pro Tyr His Asp Phe Ile Leu Glu Asp Ala Ala Ser Pro Lys
            580                 585                 590

tgc att atg aag gaa aaa aaa aag cct ggt gag act ttc ttc atg tgt     1824
Cys Ile Met Lys Glu Lys Lys Lys Pro Gly Glu Thr Phe Phe Met Cys
        595                 600                 605

tcc tgt agc tct gat gag tgc aat gac aac atc atc ttc tca gaa gaa     1872
Ser Cys Ser Ser Asp Glu Cys Asn Asp Asn Ile Ile Phe Ser Glu Glu
```

```
    610                 615                 620

tat aac acc agc aat cct gac                                         1893
Tyr Asn Thr Ser Asn Pro Asp
625                 630


<210> SEQ ID NO 2
<211> LENGTH: 631
<212> TYPE: PRT
<213> ORGANISM: Artificial Sequence
<220> FEATURE:
<223> OTHER INFORMATION: Synthetic Construct

<400> SEQUENCE: 2

Met Lys Trp Val Thr Phe Leu Leu Leu Leu Phe Ile Ser Gly Ser Ala
1               5                   10                  15

Phe Ser Ala Ala Ala Asn Gly Ala Val Lys Phe Pro Gln Leu Cys Lys
            20                  25                  30

Phe Cys Asp Val Arg Phe Ser Thr Cys Asp Asn Gln Lys Ser Cys Met
        35                  40                  45

Ser Asn Cys Ser Ile Thr Ser Ile Cys Glu Lys Pro Gln Glu Val Cys
    50                  55                  60

Val Ala Val Trp Arg Lys Asn Asp Glu Asn Ile Thr Leu Glu Thr Val
65                  70                  75                  80

Cys His Asp Pro Lys Leu Pro Tyr His Asp Phe Ile Leu Glu Asp Ala
                85                  90                  95

Ala Ser Pro Lys Cys Ile Met Lys Glu Lys Lys Lys Pro Gly Glu Thr
            100                 105                 110

Phe Phe Met Cys Ser Cys Ser Ser Asp Glu Cys Asn Asp Asn Ile Ile
        115                 120                 125

Phe Ser Glu Glu Tyr Asn Thr Ser Asn Pro Asp Gly Leu Gly Pro Val
    130                 135                 140

Glu Ser Ser Pro Gly His Gly Leu Asp Thr Ala Ala Ala Gly Pro Glu
145                 150                 155                 160

Pro Ser Thr Arg Cys Glu Leu Ser Pro Ile Asn Ala Ser His Pro Val
                165                 170                 175

Gln Ala Leu Met Glu Ser Phe Thr Val Leu Ser Gly Cys Ala Ser His
            180                 185                 190

Gly Thr Thr Gly Leu Pro Arg Glu Val His Val Leu Asn Leu Arg Ser
        195                 200                 205

Thr Asp Gln Gly Pro Gly Gln Arg Gln Arg Glu Val Thr Leu His Leu
    210                 215                 220

Asn Pro Ile Ala Ser Val His Thr His His Lys Pro Ile Val Phe Leu
225                 230                 235                 240

Leu Asn Ser Pro Gln Pro Leu Val Trp Arg Leu Lys Thr Glu Arg Leu
                245                 250                 255

Ala Ala Gly Val Pro Arg Leu Phe Leu Val Ser Glu Gly Ser Val Val
            260                 265                 270

Gln Phe Pro Ser Gly Asn Phe Ser Leu Thr Ala Glu Thr Glu Glu Arg
        275                 280                 285

Asn Phe Pro Gln Glu Asn Glu His Leu Leu Arg Trp Ala Gln Lys Glu
    290                 295                 300

Tyr Gly Ala Val Thr Ser Phe Thr Glu Leu Lys Ile Ala Arg Asn Ile
305                 310                 315                 320

Tyr Ile Lys Val Gly Glu Asp Gln Val Phe Pro Pro Thr Cys Asn Ile
                325                 330                 335
```

```
Gly Lys Asn Phe Leu Ser Leu Asn Tyr Leu Ala Glu Tyr Leu Gln Pro
            340                 345                 350

Lys Ala Ala Glu Gly Cys Val Leu Pro Ser Gln Pro His Glu Lys Glu
        355                 360                 365

Val His Ile Ile Glu Leu Ile Thr Pro Ser Ser Asn Pro Tyr Ser Ala
    370                 375                 380

Phe Gln Val Asp Ile Ile Val Asp Ile Arg Pro Ala Gln Glu Asp Pro
385                 390                 395                 400

Glu Val Val Lys Asn Leu Val Leu Ile Leu Lys Ser Lys Lys Ser Val
                405                 410                 415

Asn Trp Val Ile Lys Ser Phe Asp Val Lys Gly Asn Leu Lys Val Ile
            420                 425                 430

Ala Pro Asn Ser Ile Gly Phe Gly Lys Glu Ser Glu Arg Ser Met Thr
        435                 440                 445

Met Thr Lys Leu Val Arg Asp Asp Ile Pro Ser Thr Gln Glu Asn Leu
    450                 455                 460

Met Lys Trp Ala Leu Asp Ala Gly Tyr Arg Pro Val Thr Ser Tyr Thr
465                 470                 475                 480

Met Ala Pro Val Ala Asn Arg Phe His Leu Arg Leu Glu Asn Asn Glu
                485                 490                 495

Glu Met Arg Asp Glu Glu Val His Thr Ile Pro Pro Glu Leu Arg Ile
            500                 505                 510

Leu Leu Asp Pro Asp Lys Leu Pro Gln Leu Cys Lys Phe Cys Asp Val
        515                 520                 525

Arg Phe Ser Thr Cys Asp Asn Gln Lys Ser Cys Met Ser Asn Cys Ser
    530                 535                 540

Ile Thr Ser Ile Cys Glu Lys Pro Gln Glu Val Cys Val Ala Val Trp
545                 550                 555                 560

Arg Lys Asn Asp Glu Asn Ile Thr Leu Glu Thr Val Cys His Asp Pro
                565                 570                 575

Lys Leu Pro Tyr His Asp Phe Ile Leu Glu Asp Ala Ala Ser Pro Lys
            580                 585                 590

Cys Ile Met Lys Glu Lys Lys Lys Pro Gly Glu Thr Phe Phe Met Cys
        595                 600                 605

Ser Cys Ser Ser Asp Glu Cys Asn Asp Asn Ile Ile Phe Ser Glu Glu
    610                 615                 620

Tyr Asn Thr Ser Asn Pro Asp
625                 630


<210> SEQ ID NO 3
<211> LENGTH: 118
<212> TYPE: PRT
<213> ORGANISM: Homo sapiens

<400> SEQUENCE: 3

Asn Gly Ala Val Lys Phe Pro Gln Leu Cys Lys Phe Cys Asp Val Arg
1               5                   10                  15

Phe Ser Thr Cys Asp Asn Gln Lys Ser Cys Met Ser Asn Cys Ser Ile
            20                  25                  30

Thr Ser Ile Cys Glu Lys Pro Gln Glu Val Cys Val Ala Val Trp Arg
        35                  40                  45

Lys Asn Asp Glu Asn Ile Thr Leu Glu Thr Val Cys His Asp Pro Lys
    50                  55                  60

Leu Pro Tyr His Asp Phe Ile Leu Glu Asp Ala Ala Ser Pro Lys Cys
65                  70                  75                  80
```

```
Ile Met Lys Glu Lys Lys Lys Pro Gly Glu Thr Phe Phe Met Cys Ser
                85                  90                  95

Cys Ser Ser Asp Glu Cys Asn Asp Asn Ile Ile Phe Ser Glu Glu Tyr
            100                 105                 110

Asn Thr Ser Asn Pro Asp
        115


<210> SEQ ID NO 4
<211> LENGTH: 360
<212> TYPE: PRT
<213> ORGANISM: Rattus norvegicus

<400> SEQUENCE: 4

Gly Pro Glu Pro Ser Thr Arg Cys Glu Leu Ser Pro Ile Asn Ala Ser
1               5                   10                  15

His Pro Val Gln Ala Leu Met Glu Ser Phe Thr Val Leu Ser Gly Cys
            20                  25                  30

Ala Ser His Gly Thr Thr Gly Leu Pro Arg Glu Val His Val Leu Asn
        35                  40                  45

Leu Arg Ser Thr Asp Gln Gly Pro Gly Gln Arg Gln Arg Glu Val Thr
    50                  55                  60

Leu His Leu Asn Pro Ile Ala Ser Val His Thr His His Lys Pro Ile
65                  70                  75                  80

Val Phe Leu Leu Asn Ser Pro Gln Pro Leu Val Trp Arg Leu Lys Thr
                85                  90                  95

Glu Arg Leu Ala Ala Gly Val Pro Arg Leu Phe Leu Val Ser Glu Gly
            100                 105                 110

Ser Val Val Gln Phe Pro Ser Gly Asn Phe Ser Leu Thr Ala Glu Thr
        115                 120                 125

Glu Glu Arg Asn Phe Pro Gln Glu Asn Glu His Leu Leu Arg Trp Ala
    130                 135                 140

Gln Lys Glu Tyr Gly Ala Val Thr Ser Phe Thr Glu Leu Lys Ile Ala
145                 150                 155                 160

Arg Asn Ile Tyr Ile Lys Val Gly Glu Asp Gln Val Phe Pro Pro Thr
                165                 170                 175

Cys Asn Ile Gly Lys Asn Phe Leu Ser Leu Asn Tyr Leu Ala Glu Tyr
            180                 185                 190

Leu Gln Pro Lys Ala Ala Glu Gly Cys Val Leu Pro Ser Gln Pro His
        195                 200                 205

Glu Lys Glu Val His Ile Ile Glu Leu Ile Thr Pro Ser Ser Asn Pro
    210                 215                 220

Tyr Ser Ala Phe Gln Val Asp Ile Ile Val Asp Ile Arg Pro Ala Gln
225                 230                 235                 240

Glu Asp Pro Glu Val Val Lys Asn Leu Val Leu Ile Leu Lys Ser Lys
                245                 250                 255

Lys Ser Val Asn Trp Val Ile Lys Ser Phe Asp Val Lys Gly Asn Leu
            260                 265                 270

Lys Val Ile Ala Pro Asn Ser Ile Gly Phe Gly Lys Glu Ser Glu Arg
        275                 280                 285

Ser Met Thr Met Thr Lys Leu Val Arg Asp Asp Ile Pro Ser Thr Gln
    290                 295                 300

Glu Asn Leu Met Lys Trp Ala Leu Asp Ala Gly Tyr Arg Pro Val Thr
305                 310                 315                 320

Ser Tyr Thr Met Ala Pro Val Ala Asn Arg Phe His Leu Arg Leu Glu
```

```
                325                 330                 335

Asn Asn Glu Glu Met Arg Asp Glu Glu Val His Thr Ile Pro Pro Glu
            340                 345                 350

Leu Arg Ile Leu Leu Asp Pro Asp
        355                 360


<210> SEQ ID NO 5
<211> LENGTH: 112
<212> TYPE: PRT
<213> ORGANISM: homo sapien

<400> SEQUENCE: 5

Pro Gln Leu Cys Lys Phe Cys Asp Val Arg Phe Ser Thr Cys Asp Asn
1               5                   10                  15

Gln Lys Ser Cys Met Ser Asn Cys Ser Ile Thr Ser Ile Cys Glu Lys
            20                  25                  30

Pro Gln Glu Val Cys Val Ala Val Trp Arg Lys Asn Asp Glu Asn Ile
        35                  40                  45

Thr Leu Glu Thr Val Cys His Asp Pro Lys Leu Pro Tyr His Asp Phe
    50                  55                  60

Ile Leu Glu Asp Ala Ala Ser Pro Lys Cys Ile Met Lys Glu Lys Lys
65                  70                  75                  80

Lys Pro Gly Glu Thr Phe Phe Met Cys Ser Cys Ser Ser Asp Glu Cys
                85                  90                  95

Asn Asp Asn Ile Ile Phe Ser Glu Glu Tyr Asn Thr Ser Asn Pro Asp
            100                 105                 110


<210> SEQ ID NO 6
<211> LENGTH: 567
<212> TYPE: PRT
<213> ORGANISM: Homo sapien

<400> SEQUENCE: 6

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
```

```
            180                 185                 190

Arg Gln Gln Lys Leu Ser Ser Thr Trp Glu Thr Gly Lys Thr Arg Lys
        195                 200                 205

Leu Met Glu Phe Ser Glu His Cys Ala Ile Ile Leu Glu Asp Asp Arg
    210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
            260                 265                 270

Thr Val Ala Val Lys Ile Phe Pro Tyr Glu Glu Tyr Ala Ser Trp Lys
        275                 280                 285

Thr Glu Lys Asp Ile Phe Ser Asp Ile Asn Leu Lys His Glu Asn Ile
    290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
            340                 345                 350

Ser Leu Ala Arg Gly Ile Ala His Leu His Ser Asp His Thr Pro Cys
        355                 360                 365

Gly Arg Pro Lys Met Pro Ile Val His Arg Asp Leu Lys Ser Ser Asn
    370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
                405                 410                 415

Gly Gln Val Gly Thr Ala Arg Tyr Met Ala Pro Glu Val Leu Glu Ser
            420                 425                 430

Arg Met Asn Leu Glu Asn Val Glu Ser Phe Lys Gln Thr Asp Val Tyr
        435                 440                 445

Ser Met Ala Leu Val Leu Trp Glu Met Thr Ser Arg Cys Asn Ala Val
    450                 455                 460

Gly Glu Val Lys Asp Tyr Glu Pro Pro Phe Gly Ser Lys Val Arg Glu
465                 470                 475                 480

His Pro Cys Val Glu Ser Met Lys Asp Asn Val Leu Arg Asp Arg Gly
                485                 490                 495

Arg Pro Glu Ile Pro Ser Phe Trp Leu Asn His Gln Gly Ile Gln Met
            500                 505                 510

Val Cys Glu Thr Leu Thr Glu Cys Trp Asp His Asp Pro Glu Ala Arg
        515                 520                 525

Leu Thr Ala Gln Cys Val Ala Glu Arg Phe Ser Glu Leu Glu His Leu
    530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565


<210> SEQ ID NO 7
<211> LENGTH: 853
<212> TYPE: PRT
<213> ORGANISM: Rattus norvegicus
```

<400> SEQUENCE: 7

Met Ala Val Thr Ser His His Met Ile Pro Val Met Val Val Leu Met
1 5 10 15

Ser Ala Cys Leu Ala Thr Ala Gly Pro Glu Pro Ser Thr Arg Cys Glu
20 25 30

Leu Ser Pro Ile Asn Ala Ser His Pro Val Gln Ala Leu Met Glu Ser
35 40 45

Phe Thr Val Leu Ser Gly Cys Ala Ser Arg Gly Thr Thr Gly Leu Pro
50 55 60

Arg Glu Val His Val Leu Asn Leu Arg Ser Thr Asp Gln Gly Pro Gly
65 70 75 80

Gln Arg Gln Arg Glu Val Thr Leu His Leu Asn Pro Ile Ala Ser Val
85 90 95

His Thr His His Lys Pro Ile Val Phe Leu Leu Asn Ser Pro Gln Pro
100 105 110

Leu Val Trp His Leu Lys Thr Glu Arg Leu Ala Ala Gly Val Pro Arg
115 120 125

Leu Phe Leu Val Ser Glu Gly Ser Val Val Gln Phe Pro Ser Gly Asn
130 135 140

Phe Ser Leu Thr Ala Glu Thr Glu Glu Arg Asn Phe Pro Gln Glu Asn
145 150 155 160

Glu His Leu Leu Arg Trp Ala Gln Lys Glu Tyr Gly Ala Val Thr Ser
165 170 175

Phe Thr Glu Leu Lys Ile Ala Arg Asn Ile Tyr Ile Lys Val Gly Glu
180 185 190

Asp Gln Val Phe Pro Pro Thr Cys Asn Ile Gly Lys Asn Phe Leu Ser
195 200 205

Leu Asn Tyr Leu Ala Glu Tyr Leu Gln Pro Lys Ala Ala Glu Gly Cys
210 215 220

Val Leu Pro Ser Gln Pro His Glu Lys Glu Val His Ile Ile Glu Leu
225 230 235 240

Ile Thr Pro Ser Ser Asn Pro Tyr Ser Ala Phe Gln Val Asp Ile Ile
245 250 255

Val Asp Ile Arg Pro Ala Gln Glu Asp Pro Glu Val Val Lys Asn Leu
260 265 270

Val Leu Ile Leu Lys Cys Lys Lys Ser Val Asn Trp Val Ile Lys Ser
275 280 285

Phe Asp Val Lys Gly Asn Leu Lys Val Ile Ala Pro Asn Ser Ile Gly
290 295 300

Phe Gly Lys Glu Ser Glu Arg Ser Met Thr Met Thr Lys Leu Val Arg
305 310 315 320

Asp Asp Ile Pro Ser Thr Gln Glu Asn Leu Met Lys Trp Ala Leu Asp
325 330 335

Asn Gly Tyr Arg Pro Val Thr Ser Tyr Thr Met Ala Pro Val Ala Asn
340 345 350

Arg Phe His Leu Arg Leu Glu Asn Asn Glu Glu Met Arg Asp Glu Glu
355 360 365

Val His Thr Ile Pro Pro Glu Leu Arg Ile Leu Leu Asp Pro Asp His
370 375 380

Pro Pro Ala Leu Asp Asn Pro Leu Phe Pro Gly Glu Gly Ser Pro Asn
385 390 395 400

Gly Gly Leu Pro Phe Pro Phe Pro Asp Ile Pro Arg Arg Gly Trp Lys

```
                405                 410                 415

Glu Gly Glu Asp Arg Ile Pro Arg Pro Lys Gln Pro Ile Val Pro Ser
            420                 425                 430

Val Gln Leu Leu Pro Asp His Arg Glu Pro Glu Glu Val Gln Gly Gly
        435                 440                 445

Val Asp Ile Ala Leu Ser Val Lys Cys Asp His Glu Lys Met Val Val
    450                 455                 460

Ala Val Asp Lys Asp Ser Phe Gln Thr Asn Gly Tyr Ser Gly Met Glu
465                 470                 475                 480

Leu Thr Leu Leu Asp Pro Ser Cys Lys Ala Lys Met Asn Gly Thr His
                485                 490                 495

Phe Val Leu Glu Ser Pro Leu Asn Gly Cys Gly Thr Arg His Arg Arg
            500                 505                 510

Ser Thr Pro Asp Gly Val Val Tyr Tyr Asn Ser Ile Val Val Gln Ala
        515                 520                 525

Pro Ser Pro Gly Asp Ser Ser Gly Trp Pro Asp Gly Tyr Glu Asp Leu
    530                 535                 540

Glu Ser Gly Asp Asn Gly Phe Pro Gly Asp Gly Asp Glu Gly Glu Thr
545                 550                 555                 560

Ala Pro Leu Ser Arg Ala Gly Val Val Val Phe Asn Cys Ser Leu Arg
                565                 570                 575

Gln Leu Arg Asn Pro Ser Gly Phe Gln Gly Gln Leu Asp Gly Asn Ala
            580                 585                 590

Thr Phe Asn Met Glu Leu Tyr Asn Thr Asp Leu Phe Leu Val Pro Ser
        595                 600                 605

Pro Gly Val Phe Ser Val Ala Glu Asn Glu His Val Tyr Val Glu Val
    610                 615                 620

Ser Val Thr Lys Ala Asp Gln Asp Leu Gly Phe Ala Ile Gln Thr Cys
625                 630                 635                 640

Phe Leu Ser Pro Tyr Ser Asn Pro Asp Arg Met Ser Asp Tyr Thr Ile
                645                 650                 655

Ile Glu Asn Ile Cys Pro Lys Asp Asp Ser Val Lys Phe Tyr Ser Ser
            660                 665                 670

Lys Arg Val His Phe Pro Ile Pro His Ala Glu Val Asp Lys Lys Arg
        675                 680                 685

Phe Ser Phe Leu Phe Lys Ser Val Phe Asn Thr Ser Leu Leu Phe Leu
    690                 695                 700

His Cys Glu Leu Thr Leu Cys Ser Arg Lys Lys Gly Ser Leu Lys Leu
705                 710                 715                 720

Pro Arg Cys Val Thr Pro Asp Asp Ala Cys Thr Ser Leu Asp Ala Thr
                725                 730                 735

Met Ile Trp Thr Met Met Gln Asn Lys Lys Thr Phe Thr Lys Pro Leu
            740                 745                 750

Ala Val Val Leu Gln Val Asp Tyr Lys Glu Asn Val Pro Ser Thr Lys
        755                 760                 765

Asp Ser Ser Pro Ile Pro Pro Pro Pro Pro Gln Ile Phe His Gly Leu
    770                 775                 780

Asp Thr Leu Thr Val Met Gly Ile Ala Phe Ala Ala Phe Val Ile Gly
785                 790                 795                 800

Ala Leu Leu Thr Gly Ala Leu Trp Tyr Ile Tyr Ser His Thr Gly Glu
                805                 810                 815

Thr Ala Arg Arg Gln Gln Val Pro Thr Ser Pro Pro Ala Ser Glu Asn
            820                 825                 830
```

```
Ser Ser Ala Ala His Ser Ile Gly Ser Thr Gln Ser Thr Pro Cys Ser
        835                 840                 845

Ser Ser Ser Thr Ala
    850


<210> SEQ ID NO 8
<211> LENGTH: 850
<212> TYPE: PRT
<213> ORGANISM: Homo sapien

<400> SEQUENCE: 8

Met Thr Ser His Tyr Val Ile Ala Ile Phe Ala Leu Met Ser Ser Cys
1               5                   10                  15

Leu Ala Thr Ala Gly Pro Glu Pro Gly Ala Leu Cys Glu Leu Ser Pro
            20                  25                  30

Val Ser Ala Ser His Pro Val Gln Ala Leu Met Glu Ser Phe Thr Val
        35                  40                  45

Leu Ser Gly Cys Ala Ser Arg Gly Thr Thr Gly Leu Pro Gln Glu Val
    50                  55                  60

His Val Leu Asn Leu Arg Thr Ala Gly Gln Gly Pro Gly Gln Leu Gln
65                  70                  75                  80

Arg Glu Val Thr Leu His Leu Asn Pro Ile Ser Ser Val His Ile His
                85                  90                  95

His Lys Ser Val Val Phe Leu Leu Asn Ser Pro His Pro Leu Val Trp
            100                 105                 110

His Leu Lys Thr Glu Arg Leu Ala Thr Gly Val Ser Arg Leu Phe Leu
        115                 120                 125

Val Ser Glu Gly Ser Val Val Gln Phe Ser Ser Ala Asn Phe Ser Leu
    130                 135                 140

Thr Ala Glu Thr Glu Glu Arg Asn Phe Pro His Gly Asn Glu His Leu
145                 150                 155                 160

Leu Asn Trp Ala Arg Lys Glu Tyr Gly Ala Val Thr Ser Phe Thr Glu
                165                 170                 175

Leu Lys Ile Ala Arg Asn Ile Tyr Ile Lys Val Gly Glu Asp Gln Val
            180                 185                 190

Phe Pro Pro Lys Cys Asn Ile Gly Lys Asn Phe Leu Ser Leu Asn Tyr
        195                 200                 205

Leu Ala Glu Tyr Leu Gln Pro Lys Ala Ala Glu Gly Cys Val Met Ser
    210                 215                 220

Ser Gln Pro Gln Asn Glu Glu Val His Ile Ile Glu Leu Ile Thr Pro
225                 230                 235                 240

Asn Ser Asn Pro Tyr Ser Ala Phe Gln Val Asp Ile Thr Ile Asp Ile
                245                 250                 255

Arg Pro Ser Gln Glu Asp Leu Glu Val Val Lys Asn Leu Ile Leu Ile
            260                 265                 270

Leu Lys Cys Lys Lys Ser Val Asn Trp Val Ile Lys Ser Phe Asp Val
        275                 280                 285

Lys Gly Ser Leu Lys Ile Ile Ala Pro Asn Ser Ile Gly Phe Gly Lys
    290                 295                 300

Glu Ser Glu Arg Ser Met Thr Met Thr Lys Ser Ile Arg Asp Asp Ile
305                 310                 315                 320

Pro Ser Thr Gln Gly Asn Leu Val Lys Trp Ala Leu Asp Asn Gly Tyr
                325                 330                 335

Ser Pro Ile Thr Ser Tyr Thr Met Ala Pro Val Ala Asn Arg Phe His
```

```
            340                 345                 350

Leu Arg Leu Glu Asn Asn Glu Glu Met Gly Asp Glu Glu Val His Thr
        355                 360                 365

Ile Pro Pro Glu Leu Arg Ile Leu Leu Asp Pro Gly Ala Leu Pro Ala
    370                 375                 380

Leu Gln Asn Pro Pro Ile Arg Gly Gly Glu Gly Gln Asn Gly Gly Leu
385                 390                 395                 400

Pro Phe Pro Phe Pro Asp Ile Ser Arg Arg Val Trp Asn Glu Glu Gly
                405                 410                 415

Glu Asp Gly Leu Pro Arg Pro Lys Asp Pro Val Ile Pro Ser Ile Gln
            420                 425                 430

Leu Phe Pro Gly Leu Arg Glu Pro Glu Glu Val Gln Gly Ser Val Asp
        435                 440                 445

Ile Ala Leu Ser Val Lys Cys Asp Asn Glu Lys Met Ile Val Ala Val
    450                 455                 460

Glu Lys Asp Ser Phe Gln Ala Ser Gly Tyr Ser Gly Met Asp Val Thr
465                 470                 475                 480

Leu Leu Asp Pro Thr Cys Lys Ala Lys Met Asn Gly Thr His Phe Val
                485                 490                 495

Leu Glu Ser Pro Leu Asn Gly Cys Gly Thr Arg Pro Arg Trp Ser Ala
            500                 505                 510

Leu Asp Gly Val Val Tyr Tyr Asn Ser Ile Val Ile Gln Val Pro Ala
        515                 520                 525

Leu Gly Asp Ser Ser Gly Trp Pro Asp Gly Tyr Glu Asp Leu Glu Ser
    530                 535                 540

Gly Asp Asn Gly Phe Pro Gly Asp Met Asp Glu Gly Asp Ala Ser Leu
545                 550                 555                 560

Phe Thr Arg Pro Glu Ile Val Val Phe Asn Cys Ser Leu Gln Gln Val
                565                 570                 575

Arg Asn Pro Ser Ser Phe Gln Glu Gln Pro His Gly Asn Ile Thr Phe
            580                 585                 590

Asn Met Glu Leu Tyr Asn Thr Asp Leu Phe Leu Val Pro Ser Gln Gly
        595                 600                 605

Val Phe Ser Val Pro Glu Asn Gly His Val Tyr Val Glu Val Ser Val
    610                 615                 620

Thr Lys Ala Glu Gln Glu Leu Gly Phe Ala Ile Gln Thr Cys Phe Ile
625                 630                 635                 640

Ser Pro Tyr Ser Asn Pro Asp Arg Met Ser His Tyr Thr Ile Ile Glu
                645                 650                 655

Asn Ile Cys Pro Lys Asp Glu Ser Val Lys Phe Tyr Ser Pro Lys Arg
            660                 665                 670

Val His Phe Pro Ile Pro Gln Ala Asp Met Asp Lys Lys Arg Phe Ser
        675                 680                 685

Phe Val Phe Lys Pro Val Phe Asn Thr Ser Leu Leu Phe Leu Gln Cys
    690                 695                 700

Glu Leu Thr Leu Cys Thr Lys Met Glu Lys His Pro Gln Lys Leu Pro
705                 710                 715                 720

Lys Cys Val Pro Pro Asp Glu Ala Cys Thr Ser Leu Asp Ala Ser Ile
                725                 730                 735

Ile Trp Ala Met Met Gln Asn Lys Lys Thr Phe Thr Lys Pro Leu Ala
            740                 745                 750

Val Ile His His Glu Ala Glu Ser Lys Glu Lys Gly Pro Ser Met Lys
        755                 760                 765
```

```
Glu Pro Asn Pro Ile Ser Pro Pro Ile Phe His Gly Leu Asp Thr Leu
    770                 775                 780

Thr Val Met Gly Ile Ala Phe Ala Ala Phe Val Ile Gly Ala Leu Leu
785                 790                 795                 800

Thr Gly Ala Leu Trp Tyr Ile Tyr Ser His Thr Gly Glu Thr Ala Gly
                805                 810                 815

Arg Gln Gln Val Pro Thr Ser Pro Pro Ala Ser Glu Asn Ser Ser Ala
            820                 825                 830

Ala His Ser Ile Gly Ser Thr Gln Ser Thr Pro Cys Ser Ser Ser Ser
        835                 840                 845

Thr Ala
    850


<210> SEQ ID NO 9
<211> LENGTH: 18
<212> TYPE: PRT
<213> ORGANISM: Artificial Sequence
<220> FEATURE:
<223> OTHER INFORMATION: Synthetic peptide

<400> SEQUENCE: 9

Gly Leu Gly Pro Val Glu Ser Ser Pro Gly His Gly Leu Asp Thr Ala
1               5                   10                  15

Ala Ala


<210> SEQ ID NO 10
<211> LENGTH: 21
<212> TYPE: PRT
<213> ORGANISM: Artificial Sequence
<220> FEATURE:
<223> OTHER INFORMATION: Synthetic peptide

<400> SEQUENCE: 10

Met Lys Trp Val Thr Phe Leu Leu Leu Leu Phe Ile Ser Gly Ser Ala
1               5                   10                  15

Phe Ser Ala Ala Ala
            20
```

The invention claimed is:

1. A TGFβ-binding heterotrimeric fusion protein wherein the fusion protein has an amino acid sequence that is 90% identical to SEQ ID NO: 2.

2. The fusion protein of claim 1, further comprising an amino terminal signal sequence.

3. The fusion protein of claim 1, further comprising an amino terminal or carboxy terminal tag.

4. The fusion protein of claim 3, wherein the tag is a carboxy terminal hexa-histidine.

5. A method of treating a condition related to increased expression TGFβ comprising administering an effective amount of the fusion protein of claim 1 to subject in thereof.

6. The method of claim 5, wherein the condition is a hyperproliferative disorder.

7. The method of claim 6, wherein the hyperproliferative disorder is cancer.

8. The method of claim 5, wherein the condition is fibrosis.

9. A heterotrimeric fusion protein wherein the fusion protein has the amino acid sequence of SEQ ID NO:2.

10. The fusion protein of claim 9, further comprising an amino terminal signal sequence.

11. The fusion protein of claim 9, further comprising an amino terminal or carboxy terminal tag.

12. The fusion protein of claim 11, wherein the tag is a carboxy terminal hexa-Histidine.

*13. A fusion protein comprising, in the N-terminal to C-terminal direction:*

(*i*) *a first portion having an amino acid sequence that is at least 90% identical to the amino acid sequence of SEQ ID NO: 3;*

(*ii*) *a second portion having an amino acid sequence that is at least 90% identical to the amino acid sequence of SEQ ID NO: 4; and*

(*iii*) *a third portion having an amino acid sequence that is at least 90% identical to the amino acid sequence of SEQ ID NO: 5.*

*14. The fusion protein of claim 13, wherein the first portion has an amino acid sequence that is at least 95% identical to the amino acid sequence of SEQ ID NO: 3.*

*15. The fusion protein of claim 13, wherein the second portion has an amino acid sequence that is at least 95% identical to the amino acid sequence of SEQ ID NO: 4.*

*16. The fusion protein of claim 13, wherein the third portion has an amino acid sequence that is at least 95% identical to the amino acid sequence of SEQ ID NO: 5.*

*17. The fusion protein of claim 13, wherein the first portion has an amino acid sequence that is at least 95% identical to the amino acid sequence of SEQ ID NO: 3, the second portion has an amino acid sequence that is at least 95% identical to the amino acid sequence of SEQ ID NO: 4, and the third portion has an amino acid sequence that is at least 95% identical to the amino acid sequence of SEQ ID NO: 5.*

*18. The fusion protein of claim 13, wherein the first portion has the amino acid sequence of SEQ ID NO: 3.*

*19. The fusion protein of claim 13, wherein the second portion has the amino acid sequence of SEQ ID NO: 4.*

*20. The fusion protein of claim 13, wherein the third portion has the amino acid sequence of SEQ ID NO: 5.*

*21. The fusion protein of claim 13, wherein the first portion has the amino acid sequence of SEQ ID NO: 3, the second portion has the amino acid sequence of SEQ ID NO: 4, and the third portion has the amino acid sequence of SEQ ID NO: 5.*

*22. The fusion protein of claim 13, wherein either or both of (i) the first portion and the second portion, and (ii) the second portion and the third portion are joined to one another by way of a polypeptide linker.*

*23. The fusion protein of claim 13, further comprising an amino terminal or carboxy terminal tag.*

*24. A nucleic acid encoding the fusion protein of claim 13.*

*25. The nucleic acid of claim 24, wherein the first portion has an amino acid sequence that is at least 95% identical to the amino acid sequence of SEQ ID NO: 3.*

*26. The nucleic acid of claim 24, wherein the second portion has an amino acid sequence that is at least 95% identical to the amino acid sequence of SEQ ID NO: 4.*

*27. The nucleic acid of claim 24, wherein the third portion has an amino acid sequence that is at least 95% identical to the amino acid sequence of SEQ ID NO: 5.*

*28. The nucleic acid of claim 24, wherein the first portion has an amino acid sequence that is at least 95% identical to the amino acid sequence of SEQ ID NO: 3, the second portion has an amino acid sequence that is at least 95% identical to the amino acid sequence of SEQ ID NO: 4, and the third portion has an amino acid sequence that is at least 95% identical to the amino acid sequence of SEQ ID NO: 5.*

*29. The nucleic acid of claim 24, wherein the first portion has the amino acid sequence of SEQ ID NO: 3.*

*30. The nucleic acid of claim 24, wherein the second portion has the amino acid sequence of SEQ ID NO: 4.*

*31. The nucleic acid of claim 24, wherein the third portion has the amino acid sequence of SEQ ID NO: 5.*

*32. The nucleic acid of claim 24, wherein the first portion has the amino acid sequence of SEQ ID NO: 3, the second portion has the amino acid sequence of SEQ ID NO: 4, and the third portion has the amino acid sequence of SEQ ID NO: 5.*

*33. The nucleic acid of claim 24, wherein either or both of (i) the first portion and the second portion, and (ii) the second portion and the third portion are joined to one another by way of a polypeptide linker.*

*34. The nucleic acid of claim 24, wherein the fusion protein further comprises an amino terminal or carboxy terminal tag.*

*35. A vector comprising the nucleic acid of claim 24.*

*36. A host cell comprising the nucleic acid of claim 24.*

*37. A host cell comprising the vector of claim 35.*

*38. A method of producing the fusion protein of claim 13, the method comprising contacting a host cell with a nucleic acid encoding the fusion protein and subsequently isolating the fusion protein from the host cell.*

*39. A pharmaceutical composition comprising the fusion protein of claim 13 and one or more pharmaceutically acceptable excipients.*

*40. The pharmaceutical composition of claim 39, wherein the composition is formulated for administration to a human subject.*

*41. The pharmaceutical composition of claim 40, wherein the composition is formulated for parenteral, subcutaneous, intravenous, intramuscular, or intraperitoneal administration to the human subject.*

*42. A method of reducing or preventing binding of TGF-β to one or more endogenous TGF-β receptors in a subject, the method comprising administering to the subject the fusion protein of claim 13.*

*43. The method of claim 42, wherein the subject is a human.*

* * * * *